US012527926B2

(12) United States Patent
Li et al.

(10) Patent No.: US 12,527,926 B2
(45) Date of Patent: Jan. 20, 2026

(54) NON-COMBUSTIBLE SMOKING DEVICE AND COMPONENTS THEREOF

(71) Applicant: Altria Client Services LLC, Richmond, VA (US)

(72) Inventors: San Li, Midlothian, VA (US); Raquel Olegario, Richmond, VA (US); Richard Jupe, Richmond, VA (US); Christopher S. Tucker, Midlothian, VA (US); Barry S. Smith, Hopewell, VA (US); Edmond J. Cadieux, Mechanicsville, VA (US); David Bennett, Richmond, VA (US); Georgios D. Karles, Richmond, VA (US); Ben Ragland, Providence Force, VA (US)

(73) Assignee: Altria Client Services LLC, Richmond, VA (US)

( * ) Notice: Subject to any disclaimer, the term of this patent is extended or adjusted under 35 U.S.C. 154(b) by 774 days.

(21) Appl. No.: 17/398,466

(22) Filed: Aug. 10, 2021

(65) Prior Publication Data

US 2021/0361890 A1 Nov. 25, 2021

Related U.S. Application Data

(63) Continuation of application No. 15/147,454, filed on May 5, 2016, now Pat. No. 11,090,450.

(Continued)

(51) Int. Cl.

*A61M 15/06* (2006.01)
*A24F 40/30* (2020.01)

(Continued)

(52) U.S. Cl.

CPC ............. *A61M 15/06* (2013.01); *A24F 40/30* (2020.01); *A24F 40/42* (2020.01); *A24F 40/46* (2020.01);

(Continued)

(58) Field of Classification Search

CPC ... A61M 15/06; A61M 11/042; A24F 40/485; A24F 40/46; A24F 40/30; A24F 40/42; A24F 40/10; A24F 40/20

(Continued)

(56) References Cited

U.S. PATENT DOCUMENTS 4,393,884 A 7/1983 Jacobs
4,708,151 A 11/1987 Shelar (Continued)

FOREIGN PATENT DOCUMENTS

CA 2925645 A1 4/2015
CN 1283326 C 11/2006

(Continued)

OTHER PUBLICATIONS

CN101116542 (Year: 2024).*

(Continued)

*Primary Examiner* — Phuong T Nguyen

(74) *Attorney, Agent, or Firm* — Harness, Dickey & Pierce, P.L.C.

(57) ABSTRACT

At least one example embodiment discloses a non-combustible smoking element including a pre-vapor formulation reservoir element configured to contain a pre-vapor formulation material, a pre-vapor heating element coupled to the pre-vapor formulation reservoir element and configured to heat at least a portion of the pre-vapor formulation material into a vapor and provide the vapor to a channel, a tobacco heating element configured to heat at least a portion of tobacco and generate an aroma and a tobacco housing configured to contain the tobacco and provide the aroma to the channel.

17 Claims, 23 Drawing Sheets

Related U.S. Application Data

(60) Provisional application No. 62/260,793, filed on Nov. 30, 2015, provisional application No. 62/260,761, filed on Nov. 30, 2015, provisional application No. 62/157,496, filed on May 6, 2015.

(51) Int. Cl.

*A24F 40/42* (2020.01)
*A24F 40/46* (2020.01)
*A24F 40/485* (2020.01)
*A61M 11/04* (2006.01)
*A24F 40/10* (2020.01)
*A24F 40/20* (2020.01)

(52) U.S. Cl.

CPC ......... *A24F 40/485* (2020.01); *A61M 11/042* (2014.02); *A24F 40/10* (2020.01); *A24F 40/20* (2020.01)

(58) Field of Classification Search

USPC .......................................................... 392/404
See application file for complete search history.

(56) References Cited

U.S. PATENT DOCUMENTS 4,714,082 A 12/1987 Banerjee et al.
4,756,318 A 7/1988 Clearman et al.
4,771,796 A 9/1988 Myer
4,776,353 A * 10/1988 Lilja ...................... A24B 15/18 131/273
4,793,365 A 12/1988 Sensabaugh, Jr. et al.
4,854,331 A 8/1989 Banerjee et al.
4,911,181 A 3/1990 Vromen et al.
4,917,128 A 4/1990 Clearman et al.
4,947,874 A 8/1990 Brooks et al.
4,961,438 A 10/1990 Korte
5,020,548 A 6/1991 Farrier et al.
5,033,483 A 7/1991 Clearman et al.
5,042,509 A 8/1991 Banerjee et al.
5,060,666 A 10/1991 Clearman et al.
5,060,671 A 10/1991 Counts et al.
5,065,776 A 11/1991 Lawson et al.
5,067,499 A 11/1991 Banerjee et al.
5,076,292 A 12/1991 Sensabaugh, Jr. et al.
5,080,114 A 1/1992 Rudolph et al.
5,159,942 A 11/1992 Brinkley et al.
5,235,992 A 8/1993 Sensabaugh, Jr.
5,240,016 A 8/1993 Nichols et al.
5,293,883 A 3/1994 Edwards
5,388,594 A * 2/1995 Counts .................. A24F 40/485 131/194
5,433,224 A 7/1995 Luke et al.
5,505,214 A * 4/1996 Collins .................... A24D 1/20 131/194
5,595,706 A 1/1997 Sikka et al.
5,692,525 A * 12/1997 Counts ..................... A24D 3/17 131/194
6,234,167 B1 5/2001 Cox et al.
6,532,965 B1 3/2003 Abhulimen et al.
7,726,320 B2 6/2010 Robinson et al.
7,845,359 B2 12/2010 Montaser
8,079,371 B2 12/2011 Robinson et al.
8,479,747 B2 7/2013 O'Connell
8,528,569 B1 9/2013 Newton
8,678,012 B2 3/2014 Li et al.
8,678,013 B2 3/2014 Crooks et al.
8,714,161 B2 5/2014 Liu
8,833,364 B2 9/2014 Buchberger
8,881,737 B2 11/2014 Collett et al.
8,893,724 B2 11/2014 Woodcock et al.
8,899,238 B2 12/2014 Robinson et al.
8,997,753 B2 4/2015 Li et al.
9,004,073 B2 4/2015 Tucker et al.
9,010,335 B1 4/2015 Scatterday
9,078,473 B2 7/2015 Worm et al.
9,167,852 B2 10/2015 Xiu
9,271,528 B2 3/2016 Liu
9,289,014 B2 3/2016 Tucker et al.
9,357,803 B2 6/2016 Egoyants et al.
9,462,830 B2 10/2016 Liu
9,510,623 B2 12/2016 Tucker et al.
9,554,598 B2 1/2017 Egoyants et al.
9,609,893 B2 4/2017 Novak, III et al.
9,609,894 B2 4/2017 Abramov et al.
9,648,908 B1 5/2017 Rinehart et al.
9,668,523 B2 6/2017 Tucker et al.
9,675,117 B2 6/2017 Li et al.
9,730,473 B2 8/2017 Shinkawa et al.
9,877,516 B2 1/2018 Tucker et al.
9,974,334 B2 5/2018 Dooly et al.
9,980,523 B2 5/2018 Abramov et al.
9,999,256 B2 6/2018 Abramov et al.
10,010,109 B2 * 7/2018 Janardhan ............... A24F 40/40
10,165,797 B2 1/2019 Chen et al.
10,226,073 B2 3/2019 Bless et al.
10,375,996 B2 8/2019 Aoun et al.
10,543,323 B2 1/2020 Buchberger
10,645,976 B2 5/2020 Bless et al.
10,667,563 B2 * 6/2020 Kane ....................... A24F 40/42
2005/0172976 A1 * 8/2005 Newman .................. A24C 5/01 131/194
2007/0102013 A1 5/2007 Adams et al.
2008/0092912 A1 * 4/2008 Robinson ................ A24F 40/40 131/200
2009/0314299 A1 12/2009 Kilpatrick
2010/0200006 A1 8/2010 Robinson et al.
2011/0036363 A1 2/2011 Urtsev et al.
2012/0060853 A1 3/2012 Robinson et al.
2012/0199146 A1 8/2012 Marangos
2012/0260927 A1 * 10/2012 Liu ......................... A24F 40/46 219/525
2013/0014772 A1 * 1/2013 Liu ......................... A24F 40/30 131/329
2013/0081642 A1 4/2013 Safari
2013/0160764 A1 6/2013 Liu
2013/0160765 A1 6/2013 Liu
2013/0160780 A1 6/2013 Matsumoto et al.
2013/0167853 A1 7/2013 Liu
2013/0192615 A1 * 8/2013 Tucker .................... A24F 40/70 131/328
2013/0192616 A1 8/2013 Tucker et al.
2013/0192617 A1 8/2013 Thompson
2013/0192622 A1 8/2013 Tucker et al.
2013/0192623 A1 8/2013 Tucker et al.
2013/0220315 A1 8/2013 Conley et al.
2013/0255675 A1 10/2013 Liu
2013/0319407 A1 12/2013 Liu
2013/0319439 A1 12/2013 Gorelick et al.
2013/0333700 A1 * 12/2013 Buchberger .......... B05B 7/0012 128/203.26
2014/0000638 A1 1/2014 Sebastian et al.
2014/0036688 A1 2/2014 Stassinopoulos et al.
2014/0060527 A1 3/2014 Liu
2014/0060554 A1 3/2014 Collett et al.
2014/0060556 A1 3/2014 Liu
2014/0096781 A1 4/2014 Sears et al.
2014/0096782 A1 4/2014 Ampolini et al.
2014/0123989 A1 5/2014 LaMothe
2014/0144453 A1 5/2014 Capuano et al.
2014/0166028 A1 6/2014 Fuisz et al.
2014/0166029 A1 6/2014 Weigensberg et al.
2014/0190496 A1 7/2014 Wensley et al.
2014/0190503 A1 7/2014 Li et al.
2014/0202472 A1 7/2014 Levitz et al.
2014/0253144 A1 9/2014 Novak, III et al.
2014/0261486 A1 9/2014 Potter et al.
2014/0261487 A1 9/2014 Chapman et al.
2014/0261488 A1 * 9/2014 Tucker .................... A24F 40/50 131/328
2014/0261489 A1 9/2014 Cadieux et al.
2014/0261490 A1 9/2014 Kane
2014/0283825 A1 9/2014 Buchberger

(56) References Cited

U.S. PATENT DOCUMENTS

| | | | | |
|---|---|---|---|---|
| 2014/0299125 | A1 | 10/2014 | Buchberger | |
| 2014/0305448 | A1 | 10/2014 | Zuber et al. | |
| 2014/0305454 | A1 | 10/2014 | Rinker et al. | |
| 2014/0355969 | A1 | 12/2014 | Stern | |
| 2014/0366898 | A1* | 12/2014 | Monsees | A24F 40/30 131/329 |
| 2015/0013697 | A1 | 1/2015 | Mironov | |
| 2015/0013698 | A1 | 1/2015 | Woodcock et al. | |
| 2015/0027454 | A1 | 1/2015 | Li et al. | |
| 2015/0027455 | A1 | 1/2015 | Peleg et al. | |
| 2015/0027457 | A1 | 1/2015 | Janardhan et al. | |
| 2015/0027459 | A1 | 1/2015 | Collett et al. | |
| 2015/0027469 | A1 | 1/2015 | Tucker et al. | |
| 2015/0040930 | A1 | 2/2015 | Robinson et al. | |
| 2015/0047656 | A1 | 2/2015 | Robinson et al. | |
| 2015/0053220 | A1 | 2/2015 | Levy et al. | |
| 2015/0059787 | A1 | 3/2015 | Qiu | |
| 2015/0114409 | A1 | 4/2015 | Brammer et al. | |
| 2015/0122277 | A1 | 5/2015 | Frobisher et al. | |
| 2015/0128968 | A1 | 5/2015 | Chapman et al. | |
| 2015/0136155 | A1 | 5/2015 | Verleur et al. | |
| 2015/0136158 | A1 | 5/2015 | Stevens et al. | |
| 2015/0164147 | A1 | 6/2015 | Verleur et al. | |
| 2015/0196059 | A1 | 7/2015 | Liu | |
| 2015/0201674 | A1 | 7/2015 | Dooly et al. | |
| 2015/0282527 | A1 | 10/2015 | Henry, Jr. | |
| 2015/0282529 | A1 | 10/2015 | Li et al. | |
| 2015/0305405 | A1 | 10/2015 | Fang | |
| 2015/0335070 | A1 | 11/2015 | Sears et al. | |
| 2015/0374035 | A1 | 12/2015 | Sanchez et al. | |
| 2016/0007648 | A1 | 1/2016 | Sutton et al. | |
| 2016/0007649 | A1 | 1/2016 | Sampson et al. | |
| 2016/0044963 | A1 | 2/2016 | Saleem | |
| 2016/0073695 | A1 | 3/2016 | Sears et al. | |
| 2016/0100633 | A1 | 4/2016 | Gao | |
| 2016/0120224 | A1 | 5/2016 | Mishra et al. | |
| 2016/0157525 | A1 | 6/2016 | Tucker et al. | |
| 2016/0206003 | A1 | 7/2016 | Yamada et al. | |
| 2016/0206004 | A1 | 7/2016 | Shinkawa et al. | |
| 2016/0309788 | A1 | 10/2016 | Hawes et al. | |
| 2016/0324216 | A1* | 11/2016 | Li | A24F 40/42 |
| 2016/0353803 | A1 | 12/2016 | Fang | |
| 2016/0360785 | A1 | 12/2016 | Bless et al. | |
| 2017/0020200 | A1 | 1/2017 | Robinson et al. | |
| 2017/0049152 | A1 | 2/2017 | Liu | |
| 2017/0065000 | A1 | 3/2017 | Sears et al. | |
| 2017/0071251 | A1* | 3/2017 | Goch | A24F 40/485 |
| 2017/0135399 | A1 | 5/2017 | Gavrielov et al. | |
| 2017/0150753 | A1* | 6/2017 | Macko | H05B 1/0244 |
| 2017/0251722 | A1 | 9/2017 | Kobal et al. | |
| 2017/0258134 | A1 | 9/2017 | Kane | |
| 2017/0258137 | A1 | 9/2017 | Smith et al. | |
| 2017/0265524 | A1 | 9/2017 | Cadieux et al. | |
| 2017/0367403 | A1 | 12/2017 | Karles et al. | |
| 2018/0007971 | A1 | 1/2018 | Plojoux et al. | |
| 2018/0092400 | A1 | 4/2018 | Sahin et al. | |
| 2018/0116282 | A1 | 5/2018 | Dendy et al. | |
| 2018/0146713 | A1 | 5/2018 | Robinson et al. | |
| 2018/0177233 | A1* | 6/2018 | Tucker | A24F 40/40 |
| 2019/0159522 | A1 | 5/2019 | Bless et al. | |
| 2019/0230993 | A1* | 8/2019 | Buchberger | A61M 11/042 |
| 2021/0030061 | A1 | 2/2021 | Sahin et al. | |

FOREIGN PATENT DOCUMENTS

| | | | | |
|---|---|---|---|---|
| CN | 101277623 | A | | 10/2008 |
| CN | 201127292 | Y | | 10/2008 |
| CN | 101557728 | A | | 10/2009 |
| CN | 102264420 | A | | 11/2011 |
| CN | 102655773 | A | | 9/2012 |
| CN | 102813278 | A | | 12/2012 |
| CN | 103054196 | A | | 4/2013 |
| CN | 103179869 | A | | 6/2013 |
| CN | 203087527 | U | | 7/2013 |
| CN | 103491815 | A | | 1/2014 |
| CN | 203618787 | U | | 6/2014 |
| CN | 104219973 | A | | 12/2014 |
| CN | 104244749 | A | | 12/2014 |
| CN | 104254356 | A | | 12/2014 |
| CN | 104284606 | A | | 1/2015 |
| CN | 204146321 | U | | 2/2015 |
| CN | 104397878 | A | | 3/2015 |
| CN | 104540404 | A | | 4/2015 |
| CN | 204466906 | U | | 7/2015 |
| CN | 104853632 | A | | 8/2015 |
| CN | 105163611 | A | | 12/2015 |
| CN | 105963833 | A | | 9/2016 |
| CN | 106231937 | A | | 12/2016 |
| CN | 111990695 | A | | 11/2020 |
| DE | 202014001718 | U1 | | 5/2015 |
| EA | 019736 | | | 5/2014 |
| EA | 019736 | B1 | | 5/2014 |
| EP | 3632490 | A1 | | 4/2020 |
| EP | 3562336 | B1 | | 3/2023 |
| GB | 2513627 | A | | 11/2014 |
| JP | 2008-286510 | A | | 11/2008 |
| JP | 2010-506594 | A | | 3/2010 |
| JP | 2010206594 | A | | 9/2010 |
| JP | 2015-506170 | A | | 3/2015 |
| JP | 2017-511703 | A | | 4/2017 |
| JP | 2016571476 | | | 4/2017 |
| KR | 910002388 | A | | 2/1991 |
| KR | 930000048 | A | | 1/1993 |
| KR | 10-1999-0037661 | A | | 5/1999 |
| KR | 10-2012-0053521 | A | | 5/2012 |
| KR | 1020120053521 | | * | 5/2012 |
| KR | 10-2014-0125822 | A | | 10/2014 |
| KR | 1020140125822 | | * | 10/2014 |
| RU | 94815 | U1 | | 6/2010 |
| RU | 103281 | U1 | | 4/2011 |
| RU | 2509516 | C2 | | 3/2014 |
| TW | 201406307 | A | | 2/2014 |
| WO | WO-97/048293 | A1 | | 12/1997 |
| WO | WO-2006048774 | A1 | | 5/2006 |
| WO | WO-2008/108889 | A1 | | 9/2008 |
| WO | 2012/027350 | A2 | | 3/2012 |
| WO | WO-2014/004648 | A1 | | 1/2014 |
| WO | WO-2014116974 | A1 | | 7/2014 |
| WO | WO-2014207719 | A1 | | 12/2014 |
| WO | 2015/000974 | A1 | | 1/2015 |
| WO | 2015/038981 | A2 | | 3/2015 |
| WO | 2015046420 | A1 | | 4/2015 |
| WO | WO-2015/046385 | A1 | | 4/2015 |
| WO | WO-2015/128499 | A1 | | 9/2015 |
| WO | WO-2015/179388 | A1 | | 11/2015 |
| WO | WO-2015197852 | A2 | | 12/2015 |
| WO | WO-2016024083 | A1 | | 2/2016 |

OTHER PUBLICATIONS

CN106231937 (Year: 2024).*
DE202014001718 (Year: 2024).*
WO2014116974 (Year: 2024).*
CN104244749 (Year: 2024).*
CN104540404 (Year: 2024).*
JP2008286510 (Year: 2024).*
CN103491815 (Year: 2024).*
Decision on Grant and Search Report issued Sep. 28, 2021 in Russian Application No. 2019120820.
Korean Notice of Allowance and English translation thereof dated Oct. 17, 2023.
European Communication Pursuant to Article 94(3) mailed Aug. 18, 2022 issued in European Patent Application No. 19 205 550.7-1212.
Chinese Office Action for Application No. 202010730881.8, dated Mar. 22, 2023, with English Translation.
Korean Office Action for Application No. 10-2017-7035249, dated Apr. 12, 2023.
Korean Office Action for Application No. 10-2018-7013323, dated Jul. 14, 2023, with English Translation.
U.S. Notice of Allowance for U.S. Appl. No. 17/225,317, dated Aug. 15, 2023.

(56) References Cited

OTHER PUBLICATIONS

Chinese Rejection Decision for corresponding Application No. 201780075252.2, dated Jan. 12, 2023, and English Translation included.
Korean Office Action for corresponding Application No. 10-2019-7016963, dated Feb. 14, 2023, with English translation included herewith.
U.S. Office Action for U.S. Appl. No. 17/225,317, dated Feb. 28, 2023.
"How to Brew Your Own Tobacco E-Liquids," Vape Squad, http://www.vapesquad.com/how-to-brew-your-own-tobacco-e-liquids/, Jun. 20, 2013.
"Mixing of e-liquids," Naturally Extracted Tobacco, LLC, http://www.naturally-extracted-tobacco.com/Mixing-s/1822.htm, Jul. 6, 2013.
"Marlboro HeatStick," http://www.dailymail.co.uk/news/article-2671505/Philip-Morris-Intl-sell-Marlboro-HeatSticks.html, Jun. 26, 2014.
"White, Black 350MAH Dry Herb Vaporizers/Wax Oil Vaporier with LCD Screen," E-Cig Mechanical Mods, http://www.ecigmechanicalmods.com/sale-3013923-white-black-350mah-dry-herb-vaporizers-wax-oil-vaporizer-with-les-screen.html, Jun. 26, 2015.
"Dry Herb Vaporizer used for e-solid/Tobacco/herbs eGO electronic cigarette," HongKong Chiamey Enterprise, http://elite-electronic-cigarettes.sell.curiousexpeditions.org/iz537e0d6-dry-herb-vaporizer-uder-for-e-solid-tobacco-herbs-ego-electronic-cigarette-images, Jun. 26, 2015.
"New 10g E-Solid Tobacco Flavor Solid Electronic Cigarette Oil," eliquidtrade, Aug. 31, 2014.
International Search Report and Written Opinion dated Sep. 30, 2016 issued in International Application No. PCT/US2016/030957.
International Search Report and Written Opinion dated Feb. 14, 2017 issued in International Application No. PCT/EP2016/079344.
International Preliminary Report on Patentability dated Nov. 7, 2017 issued in International Application No. PCT/US2016/030957.
U.S. Office Action for corresponding U.S. Appl. No. 15/391,926 mailed May 25, 2018.
International Search Report and Written Opinion issued Mar. 19, 2018 in International Application No. PCT/EP2017/084705.
International Search Report dated Aug. 2, 2016 issued in International Application No. PCT/US2016/030957.
Non-Final Office Action issued Sep. 27, 2018 in U.S. Appl. No. 15/147,454.
European Communication issued Oct. 16, 2018 in European Application No. 16725284.0.
U.S. Notice of Allowance for corresponding U.S. Appl. No. 15/391,926 mailed Dec. 19, 2018.
International Preliminary Report on Patentability issued Dec. 14, 2018 in International Application No. PCT/EP2017/084705.
Final Office Action issued Apr. 2, 2019 in U.S. Appl. No. 15/147,454.
Eurasian Official Notification issued Apr. 18, 2019 in Eurasian Patent Application No. 201792210.
U.S. Notice of Allowance for corresponding U.S. Appl. No. 15/391,926 mailed May 20, 2019.
European Office Action mailed Jun. 17, 2019 in European Application No. 16802118.6.
European Office Action mailed Jun. 17, 2019 in European Application No. 16805093.8.
Chinese Office Action and English translation thereof dated Sep. 9, 2019.
Extended European Search report issued on Feb. 13, 2020 in European Application No. 19205550.7.
Russian Notice of Allowance and Search Report dated Jan. 30, 2020 issued in Russian Patent Application No. 2018123174/12(036715).
Extended European Search Report dated Mar. 12, 2020 issued in European Patent Application No. 19205549.9-1122.
Non-Final Office Action issued Dec. 2, 2019 in U.S. Appl. No. 15/147,454.
Japanese Office Action dated Mar. 2, 2020 issued in corresponding Japanese Application No. 2018-546764.
Office Action and Search Report issued Mar. 18, 2020 in Russian Application No. 2018122814.
Russian Office Action dated Mar. 18, 2020 issued in Russian Patent Application No. 2018122814. English translation provided.
Russian Search Report dated Mar. 18, 2020 issued in Russian Patent Application No. 2018122814. English translation provided.
Ukrainean Office Action dated Apr. 7, 2020 issued in Ukrainean Patent Application No. a201710730. English translation provided.
Chinese Office Action dated May 15, 2020 issued in Chinese Patent Application No. 201680026260.3. English translation provided.
Decision to Grant dated May 26, 2020 issued in Russian Patent Application No. 2018122814. English translation provided.
Russian Notice of Allowance dated May 25, 2020 issued in corresponding Russian Patent Application No. 2018122814/14(036083). English translation has been provided.
Japanese Office Action dated Jun. 9, 2020 issued in corresponding Japanese Application No. 2017-557358.
Final Office Action issued Jun. 10, 2020 in U.S. Appl. No. 15/147,454.
Japanese Office Action dated Jun. 9, 2020 issued in corresponding Japanese Patent Application No. 2017-557358. English translation has been provided.
Office Action issued May 20, 2020 in Chinese Patent Application No. 201680064436.4.
Office Action issued May 20, 2020 in Chinese Patent Application No. 201680064434.5.
Written Opinion of the international Preliminary Examining Authority dated Nov. 7, 2017 issued in corresponding International Application No. PCT/EP2016/079344.
European Communication issued Jul. 21, 2020 in European Application No. 17823175.9.
First Office Action issued Jul. 29, 2020 in Israel Application No. 255240.
Final Office Action issued on Sep. 2, 2020 in U.S. Appl. No. 15/147,454.
Communication pursuant to Article 94(3) EPC issued Oct. 27, 2020 in European Application No. 17 823175.9.
Notice of Grounds for Rejection issued Nov. 9, 2020 in Japanese Application No. P 2018-546764.
Notice of Grounds for Rejection dated Nov. 16, 2020 issued in Japanese Patent Application No. P2018-546765.
U.S. Office Action dated Jun. 25, 2020 issued in co-pending U.S. Appl. No. 16/299,557.
Non-Final Office Action issued Jun. 25, 2020 in U.S. Appl. No. 16/299,557.
Notice of Allowance issued Jan. 8, 2021 in U.S. Appl. No. 16/299,557.
U.S. Notice of Allowance dated Jan. 8, 2021 issued in co-pending U.S. Appl. No. 16/299,557.
Notice of Allowance issued Apr. 21, 2021 in U.S. Appl. No. 15/147,454.
Mexican Office Action for Application No. MX/a/2019/007580, dated Apr. 25, 2023.
Communication pursuant to Article 94(3) EPC issued Nov. 9, 2021 in European Application No. 17 823 175.9.
Decision to Grant issued Sep. 13, 2021 in Japanese Application No. 2018-546764.
Korean Notice of Allowance for corresponding Application No. 10-2019-7016963, dated Apr. 25, 2023, with English translation included herewith.
First Official Notification issued Jul. 19, 2021 in Israeli Patent Application No. 279264.
First Official Notification issued Jul. 19, 2021 in Israeli Patent Application No. 279263.
Korean Office Action and English translation thereof dated Aug. 8, 2023.
Korean Notice of Allowance for Korean Application No. 10-2018-7013478 and English translation thereof mailed Jan. 26, 2024.
Chinese Office Action for Chinese Application No. 202010730881.8 and English translation thereof mailed Feb. 1, 2024.
Chinese Office action for Application No. 202010730885.6, dated Feb. 1, 2024, with English Translation included herewith.
Office Action issued Aug. 27, 2021 in Chinese Application No. 201780075252.2.

(56) References Cited

OTHER PUBLICATIONS

Chinese Office Action and English translation thereof dated May 12, 2022 issued in Chinese Application No. 201780075252.2.
Chinese Office Action and English translation thereof dated Feb. 10, 2022 for Chinese Patent Application No. 201780075252.2.
European Intention to Grant mailed Sep. 27, 2022.
Japanese Decision to Grant and English translation thereof dated Oct. 11, 2022.
Japanese Notice of Allowance for corresponding Application No. 2021-185202, dated Apr. 27, 2023, with English translation.
Chinese Office action for Application No. 202010730885.6, dated Apr. 7, 2023, with English Translation included herewith.
English translation of Japanese Office Action mailed Jan. 4, 2022 issued in Japanese Patent Application No. 2019-531464.
Chinese Office Action for Chinese Application No. 202110358775.6 and English translation thereof dated Nov. 8, 2023.
Chinese Office Action for Chinese Application No. 202010730881.8 and English translation thereof mailed Nov. 4, 2023.
Chinese Office action for Application No. 202010730885.6, dated Apr. 27, 2024, with English Translation included herewith.
European Office Action for Application No. 19205550.7, dated Apr. 3, 2024.
Korean Office Action for Application No. 1020247000996, dated Dec. 11, 2024, with English translation.
Malaysian Office Action for Application No. PI2022001904, dated Apr. 11, 2025.
Malaysian Office Action for Application No. PI2022001916, dated Apr. 11, 2025.
Ukrainian Office Action for Application No. a202003705, dated Oct. 14, 2024, with English translation.
Ukrainian Office Action for Application No. a202003711, dated Oct. 14, 2024, with English translation.
European Notice of Allowance for Application No. 19205550.7, dated Nov. 18, 2024.
U.S. Office Action for U.S. Appl. No. 18/519,406, dated Dec. 4, 2024.
U.S. Office Action for U.S. Appl. No. 18/519,406, dated May 9, 2025.
Partial Eurpoean Search Report for Application No. 25170019.1, dated Aug. 1, 2025.
Korean Notice of Allowance for Application No. 1020247000996, dated Jul. 15, 2025.
U.S. Notice of Allowance for corresponding U.S. Appl. No. 18/519,406 mailed Oct. 29, 2025.
Extended European Search Report for European Application No. 25170019.1 mailed Oct. 23, 2025.
Office Action for European Application No. 25170019.1 dated Dec. 1, 2025.

* cited by examiner

NON-COMBUSTIBLE SMOKING DEVICE AND COMPONENTS THEREOF

PRIORITY

This non-provisional patent application is a continuation of U.S. application Ser. No. 15/147,454, filed on May 5, 2016, which claims priority under 35 U.S.C. § 119(e) to provisional U.S. application Nos. 62/157,496 filed on May 6, 2015, 62/260,793 filed on Nov. 30, 2015 and 62/260,761 filed on Nov. 30, 2015, all in the United States Patent and Trademark Office, the entire contents of each of which are incorporated herein by reference.

BACKGROUND

Field

At least some example embodiments relate generally to a non-combustible smoking device.

Related Art

Electronic vaping devices are used to vaporize a pre-vapor formulation into a vapor. These electronic vaping devices may be referred to as e-vaping devices. E-vaping devices include a heater, which vaporizes the pre-vapor formulation to produce the vapor. The e-vaping device may include several e-vaping elements including a power source, a cartridge or e-vaping tank including the heater and a reservoir capable of holding the pre-vapor formulation.

SUMMARY

At least one example embodiment relates to a non-combustible smoking device. A non-combustible smoking device may have a heater that heats a pre-vapor formulation and may provide heat to a tobacco element that receives the vapor. More specifically, the non-combustible smoke device according to example embodiments exposes a vapor to a tobacco element and/or exposes a pre-vapor formulation to a tobacco element.

At least one example embodiment discloses a non-combustible smoking element including a pre-vapor formulation reservoir element configured to contain a pre-vapor formulation material, a pre-vapor heating element coupled to the pre-vapor formulation reservoir element and configured to heat at least a portion of the pre-vapor formulation material into a vapor and provide the vapor to a channel, a tobacco heating element configured to heat at least a portion of tobacco and generate an aroma and a tobacco housing configured to contain the tobacco and provide the aroma to the channel.

In an example embodiment, the tobacco heating element includes a plurality of heaters in the tobacco housing.

In an example embodiment, the plurality of heaters are upstream from the pre-vapor heating element.

In an example embodiment, the plurality of heaters are outside the channel and the pre-vapor heating element is in the channel.

In an example embodiment, the tobacco housing includes an outer housing extending in a longitudinal direction and an inner tube in the outer housing and extending in the longitudinal direction, a space between the outer housing and the inner tube defining a space to contain the tobacco.

In an example embodiment, the tobacco heating element is a coil and extends around the inner tube.

In an example embodiment, the tobacco heating element extends around the inner tube at an interval of 1-2 millimeters.

In an example embodiment, the tobacco housing includes a connecting piece at a first end of the tobacco housing, the connecting piece including at least one first air inlet to provide air to the space between the outer housing and the inner tube.

In an example embodiment, the connecting piece includes a second air inlet to provide air within the inner tube.

At least one example embodiment discloses a non-combustible smoking element including a pre-vapor formulation reservoir element configured to contain a pre-vapor formulation material, the pre-vapor formulation reservoir element defining a channel through the pre-vapor formulation reservoir element, a heating element coupled to the pre-vapor formulation reservoir element and configured to heat at least a portion of the pre-vapor formulation material into a vapor and provide the vapor to a first portion of the channel and a tobacco element at a second portion of the channel and positioned to receive the vapor.

In an example embodiment, the heating element is in the channel.

In an example embodiment, the tobacco element is downstream from the heating element.

In an example embodiment, the heating element is configured to heat the tobacco at a maximum of 200 degrees Celsius.

In an example embodiment, the heating element is separated from the tobacco element by less than thirty millimeters.

In an example embodiment, the pre-vapor formulation reservoir element includes an outer housing configured to contain the pre-vapor formulation material, an inner tube of the outer housing defining the channel, and the tobacco element is between the heating element and an end of the inner tube.

At least one example embodiment discloses a non-combustible smoking element including a pre-vapor formulation reservoir element configured to contain a pre-vapor formulation material, a heating element coupled to the pre-vapor formulation reservoir element and configured to heat at least a portion of the pre-vapor formulation material into a vapor and provide the vapor to a first channel and a tobacco containing element defining at least a portion of the first channel, the tobacco containing element overlapping at least a portion of the heating element, the tobacco containing element being arranged to receive the vapor.

In an example embodiment, the tobacco containing element is an annular sleeve.

In an example embodiment, the tobacco containing element includes an inner wall and an outer wall, the inner wall being permeable and the outer wall being impermeable.

In an example embodiment, the non-combustible smoking element includes an outer wall element on the tobacco containing element, the outer wall element including an outer wall part and an inner wall part, the outer wall part and the tobacco containing element defining portions of a second air channel.

In an example embodiment, the outer wall element includes a cover at a first end of the inner wall part, the cover covering the first channel.

BRIEF DESCRIPTION OF THE DRAWINGS

The above and other features and advantages of example embodiments will become more apparent by describing in detail, example embodiments with reference to the attached drawings. The accompanying drawings are intended to depict example embodiments and should not be interpreted to limit the intended scope of the claims. The accompanying drawings are not to be considered as drawn to scale unless explicitly noted.

DETAILED DESCRIPTION

Figure 1A:
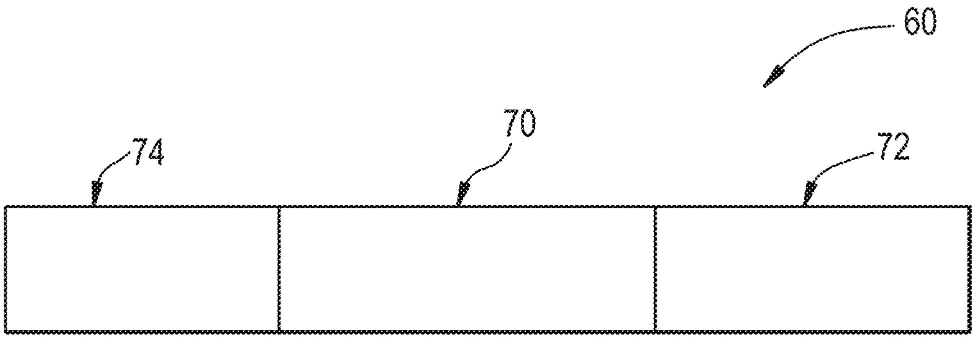
FIGS. 1A-1B illustrate a non-combustible smoking device including a tobacco element, in accordance with an example embodiment.

Some detailed example embodiments are disclosed herein. However, specific structural and functional details disclosed herein are merely representative for purposes of describing example embodiments. Example embodiments may, however, be embodied in many alternate forms and should not be construed as limited to only the embodiments set forth herein.

Accordingly, while example embodiments are capable of various modifications and alternative forms, embodiments thereof are shown by way of example in the drawings and will herein be described in detail. It should be understood, however, that there is no intent to limit example embodiments to the particular forms disclosed, but to the contrary, example embodiments are to cover all modifications, equivalents, and alternatives falling within the scope of example embodiments. Like numbers refer to like elements throughout the description of the figures.

It should be understood that when an element or layer is referred to as being "on," "connected to," "coupled to," or "covering" another element or layer, it may be directly on, connected to, coupled to, or covering the other element or layer or intervening elements or layers may be present. In contrast, when an element is referred to as being "directly on," "directly connected to," or "directly coupled to" another element or layer, there are no intervening elements or layers present. Like numbers refer to like elements throughout the specification. As used herein, the term "and/or" includes any and all combinations of one or more of the associated listed items.

It should be understood that, although the terms first, second, third, etc. may be used herein to describe various elements, elements, regions, layers and/or sections, these elements, elements, regions, layers, and/or sections should not be limited by these terms. These terms are only used to distinguish one element, element, region, layer, or section from another region, layer, or section. Thus, a first element, element, region, layer, or section discussed below could be termed a second element, element, region, layer, or section without departing from the teachings of example embodiments.

Spatially relative terms (e.g., "beneath," "below," "lower," "above," "upper," and the like) may be used herein for ease of description to describe one element or feature's relationship to another element(s) or feature(s) as illustrated in the figures. It should be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the term "below" may encompass both an orientation of above and below. The device may be otherwise oriented (rotated 90 degrees or at other orientations) and the spatially relative descriptors used herein interpreted accordingly.

The terminology used herein is for the purpose of describing various embodiments only and is not intended to be limiting of example embodiments. As used herein, the singular forms "a," "an," and "the" are intended to include the plural forms as well, unless the context clearly indicates otherwise. It will be further understood that the terms "includes," "including," "comprises," and/or "comprising," when used in this specification, specify the presence of stated features, integers, steps, operations, elements, and/or elements, but do not preclude the presence or addition of one or more other features, integers, steps, operations, elements, elements, and/or groups thereof.

Example embodiments are described herein with reference to cross-sectional illustrations that are schematic illustrations of idealized embodiments (and intermediate structures) of example embodiments. As such, variations from the shapes of the illustrations as a result, for example, of manufacturing techniques and/or tolerances, are to be expected. Thus, example embodiments should not be construed as limited to the shapes of regions illustrated herein but are to include deviations in shapes that result, for example, from manufacturing. Thus, the regions illustrated in the figures are schematic in nature and their shapes are not intended to illustrate the actual shape of a region of a device and are not intended to limit the scope of example embodiments.

Unless otherwise defined, all terms (including technical and scientific terms) used herein have the same meaning as commonly understood by one of ordinary skill in the art to which example embodiments belong. It will be further understood that terms, including those defined in commonly used dictionaries, should be interpreted as having a meaning that is consistent with their meaning in the context of the relevant art and will not be interpreted in an idealized or overly formal sense unless expressly so defined herein.

FIG. 1A illustrates a non-combustible smoking device 60 according to an example embodiment. The non-combustible smoking device 60 includes a replaceable cartridge (or first section) 70, a reusable fixture (or second section) 72 and a tobacco containing section (or third section) 74.

Figure 1B:
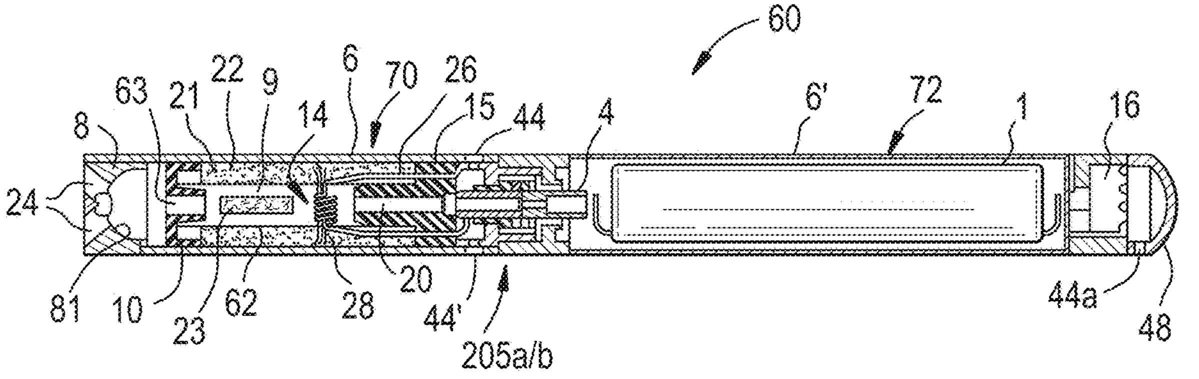

FIG. 1B illustrates a cross-sectional view of the non-combustible smoking device 60 according to an example embodiment. The non-combustible smoking device 60 comprises a replaceable cartridge (or first section) 70 and a reusable fixture (or second section) 72, which are coupled together at a connection 205*a/b* (e.g., 205*a* is a male threaded connection on cartridge 70, and 205*b* is a female threaded connection on reusable fixture 72) or by other convenience such as a snug-fit, detent, clamp and/or clasp. The first section 70 includes an outer tube 6 (or housing) extending in a longitudinal direction and an inner tube 62 coaxially positioned within the outer tube or housing 6. The inner tube 62 defines an outer air passage (or channel) 9. Within the outer air passage 9 and downstream from a heater 14 is a tobacco element 23. The tobacco element 23 may be in a porous aluminum tube or processed/shaped in a porous form.

The term "tobacco element" may refer to any tobacco plant material including tobacco leaf, tobacco plug, reconstituted tobacco, compressed tobacco rod, shaped, or powder, for example.

The tobacco element 23 may also be wrapped in tobacco such as a tobacco sheet, a reconstituted tobacco leaf or a cigar wrapper.

The second section 72 can also include an outer tube 6' (or housing) extending in a longitudinal direction. In an alternative embodiment, the outer tube 6 and 6' can be a single tube housing both the first section 70 and the second section 72 and the entire non-combustible smoking device 60 can be disposable.

The non-combustible smoking device 60 can also include a central air passage 20 defined in part by the inner tube 62 and an upstream seal 15. Moreover, the non-combustible smoking device 60 includes a pre-vapor formulation supply reservoir 22. The pre-vapor formulation supply reservoir 22 comprises a pre-vapor formulation material and optionally a pre-vapor formulation storage medium 21 operable to store the pre-vapor formulation material therein.

In an embodiment, the pre-vapor formulation supply reservoir 22 is contained in an outer annulus between the outer tube 6 and the inner tube 62. The annulus is sealed at an upstream end by the seal 15 and by a pre-vapor formulation gasket 10 at a downstream end so as to prevent leakage of the pre-vapor formulation material from the pre-vapor formulation supply reservoir 22.

In an embodiment, a heater 14 is also contained in the inner tube 62 downstream of and in spaced apart relation to the portion of central air passage 20 defined by the seal 15. The heater 14 can be in the form of a wire coil, a planar body, a ceramic body, a single wire, a cage of resistive wire or any other suitable form.

A wick 28 is in communication with the pre-vapor formulation material in the pre-vapor formulation supply reservoir 22 and in communication with the heater 14 such that the wick 28 disposes pre-vapor formulation material in proximate relation to the heater 14. The wick 28 may be constructed of a fibrous and flexible material. The wick 28 may include at least one filament having a capacity to draw a pre-vapor formulation. For example, the wick 28 may comprise a bundle of filaments which may include glass (or ceramic) filaments. In another embodiment, a bundle comprising a group of windings of glass filaments, for example, three of such windings, all which arrangements are capable of drawing pre-vapor formulation via capillary action via interstitial spacing between the filaments.

A power supply 1 in the second section 72 may be operably connected to the heater 14 (as described below) to apply voltage across the heater 14. The non-combustible smoking device 60 also includes at least one air inlet 44 operable to deliver air to the central air passage 20 and/or other portions of the inner tube 62.

Figure 2A:
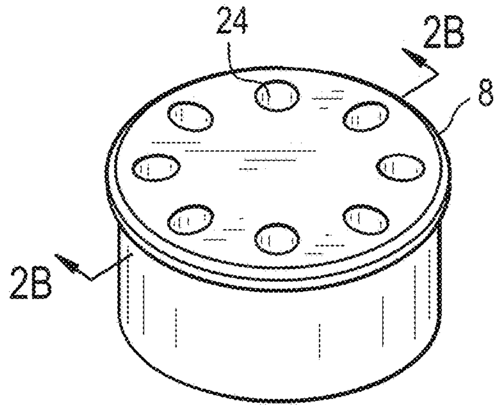
FIG. 2A is a perspective view of a mouth-end insert for use with the non-combustible smoking device of FIG. 1A, in accordance with an example embodiment.
Figure 2B:
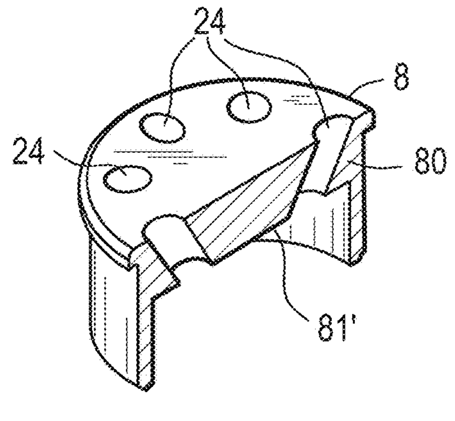
FIG. 2B is a cross-sectional view along line B-B of the mouth-end insert of FIG. 2A, in accordance with an example embodiment.

As shown in FIGS. 1-2B, the non-combustible smoking device 60 further includes a mouth-end insert 8 having at least two off-axis, diverging outlets 24. The mouth-end insert 8 is in fluid communication with the central air passage 20 via the interior of inner tube 62 and a central passage 63, which extends through the gasket 10.

Moreover, the heater 14 extends in a direction transverse to the longitudinal direction and heats the pre-vapor formulation material to a temperature sufficient to vaporize the pre-vapor formulation material and form a vapor. In other embodiments, the heater 14 may be arranged in another manner such as in the longitudinal direction.

The vapor then flows into the tobacco element 23 upon an applying a negative pressure on the mouth-end insert 8. The heater 14 may be a set distance from the tobacco element 23 or contacting the tobacco element 23 such that the heater 14 heats the tobacco element 23 during application of a negative pressure. For example, the heater 14 may be ten (10) millimeters or less from the tobacco element 23. The heater 14 may be arranged to produce a temperature of 50 degrees Celsius at the mouth-end insert 8. Moreover, the heater 14 may heat the tobacco element 23 to a temperature between 50 and 200 degrees Celsius and heat the pre-vapor formulation at 400 degrees Celsius.

The heater 14 warms the tobacco element 23, but does not burn the tobacco. Thus, the warming of the tobacco element 23 may be referred to as non-combustible. Because the section 70 includes the tobacco element 23 and the heater 14, the section 70 may be referred to as a non-combustible smoking element.

Referring to FIG. 1, the wick 28, pre-vapor formulation supply reservoir 22 and mouth-end insert 8 are contained in the cartridge 70 and the power supply 1 is contained in the second section 72. In one embodiment, the first section (the cartridge) 70 is disposable and the second section (the fixture) 72 is reusable. The sections 70, 72 can be attached by a threaded connection 205, as described above, whereby the downstream section 70 can be replaced when the pre-vapor formulation supply reservoir 22 is used up. Having a separate first section 70 and second section 72 provides a number of advantages. First, if the first section 70 contains the at least one heater 14, the pre-vapor formulation supply reservoir 22 and the wick 28, all elements which are potentially in contact with the pre-vapor formulation are disposed of when the first section 70 is replaced. Thus, there will be no cross-contamination between different mouth-end inserts 8, for example, when using different pre-vapor formulation materials. Also, if the first section 70 is replaced at suitable intervals, there is little chance of the heater becoming clogged with pre-vapor formulation. Optionally, the first section 70 and the second section 72 are arranged to lock together when engaged.

In an embodiment, the at least one air inlet 44 includes one or two air inlets 44, 44'. Alternatively, there may be three, four, five or more air inlets. If there is more than one air inlet 44, 44', the air inlets 44, 44' are located at different locations along the non-combustible smoking device 60. For example, as shown in FIG. 1, an air inlet **44*a* can be positioned at the upstream end of the non-combustible smoking device 60 adjacent a sensor 16 such that the sensor 16 supplies power to the heater 14 upon sensing an application of a negative pressure. Air inlet 44*a* should communicate with the mouth-end insert 8 so that a draw upon the mouth-end insert activates the sensor 16. The air from the air inlet 44*a* can then flow along the power supply 1 and to the central air passage 20 in the seal 15 and/or to other portions of the inner tube 62 and/or outer tube 6. At least one additional air inlet 44, 44' can be located adjacent and upstream of the seal 15 or at any other desirable location. Altering the size and number of air inlets 44, 44' can also aid in establishing the resistance to draw of the non-combustible smoking device 60**.

In an embodiment, the heater 14 is arranged to communicate with the wick 28 and to heat the pre-vapor formulation material contained in the wick 28 to a temperature sufficient to vaporize the pre-vapor formulation material and form a vapor.

The heater 14 may be a wire coil surrounding wick 28. Examples of suitable electrically resistive materials include titanium, zirconium, tantalum and metals from the platinum group. Examples of suitable metal alloys include stainless steel, nickel-, cobalt-, chromium-, aluminium- titanium-zirconium-, hafnium-, niobium-, molybdenum-, tantalum-, tungsten-, tin-, gallium-, manganese- and iron-containing alloys, and super-alloys based on nickel, iron, cobalt, stainless steel. For example, the heater may be formed of nickel aluminides, a material with a layer of alumina on the surface, iron aluminides and other composite materials, the electrically resistive material may optionally be embedded in, encapsulated or coated with an insulating material or vice-versa, depending on the kinetics of energy transfer and the external physicochemical properties required. In one embodiment, the heater 14 comprises at least one material selected from the group consisting of stainless steel, copper, copper alloys, nickel-chromium alloys, superalloys and combinations thereof. In an embodiment, the heater 14 is formed of nickel-chromium alloys or iron-chromium alloys. In one embodiment, the heater 14 can be a ceramic heater having an electrically resistive layer on an outside surface thereof.

In another embodiment, the heater 14 may be constructed of an iron-aluminide (e.g., FeAl or Fe.sub.3Al), such as those described in commonly owned U.S. Pat. No. 5,595,706 to Sikka et al. filed Dec. 29, 1994, or nickel aluminides (e.g., Ni.sub.3Al). Use of iron-aluminides is particularly advantageous in that they exhibit high resistivity. FeAl exhibits a resistivity of approximately 180 micro-ohms, whereas stainless steel exhibits approximately 50 to 91 micro-ohms. The higher resistivity lowers current draw or load on the power source (battery) 1.

In one embodiment, the heater 14 comprises a wire coil which at least partially surrounds the wick 28. In that embodiment, the wire may be a metal wire and/or the heater coil that extends partially along the length of the wick 28. The heater coil may extend fully or partially around the circumference of the wick 28. In another embodiment, the heater coil is not in contact with the wick 28.

The heater 14 heats the pre-vapor formulation in the wick 28 by thermal conduction. Alternatively, heat from the heater 14 may be conducted to the pre-vapor formulation by means of a heat conductive element or the heater 14 may transfer heat to the incoming ambient air that is drawn through the non-combustible smoking device 60 during use, which in turn heats the pre-vapor formulation by convection.

In one embodiment, the wick comprises a ceramic material or ceramic fibers. As noted above, the wick 28 is at least partially surrounded by the heater 14. Moreover, in an embodiment, the wick 28 extends through opposed openings in the inner tube 62 such that end portions 29, 31 of the wick 28 are in contact with the pre-vapor formulation supply reservoir 22.

The wick 28 may comprise a plurality or bundle of filaments. In one embodiment, the filaments may be generally aligned in a direction transverse to the longitudinal direction of the non-combustible smoking device 60, but example embodiments are not limited to this orientation. In one embodiment, the structure of the wick 28 is formed of ceramic filaments capable of drawing the pre-vapor formulation via capillary action via interstitial spacing between the filaments to the heater 14. The wick 28 can include filaments having a cross-section which is generally cross-shaped, clover-shaped, Y-shaped or in any other suitable shape.

The wick 28 includes any suitable material or combination of materials. Examples of suitable materials are glass filaments and ceramic or graphite based materials. Moreover, the wick 28 may have any suitable capillarity to accommodate pre-vapor formulations having different physical properties such as density, viscosity, surface tension and vapor pressure. The capillary properties of the wick 28, combined with the properties of the pre-vapor formulation, ensure that the wick 28 is always wet in the area of the heater 14 to avoid overheating of the heater 14.

Instead of using a wick, the heater can be a porous material of sufficient capillarity and which incorporates a resistance heater formed of a material having a high electrical resistance capable of generating heat quickly.

In one embodiment, the wick 28 and the pre-vapor formulation storage medium 21 of the pre-vapor formulation supply reservoir 22 are constructed from an alumina ceramic. In another embodiment, the wick 28 includes glass fibers and the pre-vapor formulation storage medium 21 includes a cellulosic material or polyethylene terephthalate.

In an embodiment, the power supply 1 may include a battery arranged in the non-combustible smoking device 60 such that the anode is downstream of the cathode. An anode connector 4 contacts the downstream end of the battery. The heater 14 is connected to the battery by two spaced apart electrical leads.

The connection between the uncoiled, end portions 27, 27' (see FIG. 4) of the heater 14 and the electrical leads are highly conductive and temperature resistant while the heater 14 is highly resistive so that heat generation occurs primarily along the heater 14 and not at the contacts.

The battery may be a Lithium-ion battery or one of its variants, for example a Lithium-ion polymer battery. Alternatively, the battery may be a Nickel-metal hydride battery, a Nickel cadmium battery, a Lithium-manganese battery, a Lithium-cobalt battery or a fuel cell. In that case, the non-combustible smoking device 60 is usable until the energy in the power supply is depleted. Alternatively, the power supply 1 may be rechargeable and include circuitry allowing the battery to be chargeable by an external charging device. In that case, the circuitry, when charged, provides power for a desired (or alternatively a pre-determined) number of applications of negative pressure, after which the circuitry must be re-connected to an external charging device.

The non-combustible smoking device 60 also includes control circuitry including the sensor 16. The sensor 16 is operable to sense an air pressure drop and initiate application of voltage from the power supply 1 to the heater 14. The control circuitry can also include a heater activation light 48 operable to glow when the heater 14 is activated. In one embodiment, the heater activation light 48 comprises a heater activation light (e.g., a light emitting diode (LED)) 48 and is at an upstream end of the non-combustible smoking device 60 so that the heater activation light 48 takes on the appearance of a burning coal during an application of a negative pressure. Moreover, the heater activation light 48 can be arranged to be visible to the adult vaper. In addition, the heater activation light 48 can be utilized for e-vaping system diagnostics. The light 48 can also be configured such that the adult vaper can activate and/or deactivate the light 48 for privacy, such that the light 48 would not activate during vaping if desired.

The at least one air inlet 44*a* is located adjacent the sensor 16, such that the sensor 16 senses air flow indicative of a negative pressure and activates the power supply 1 and the heater activation light 48 to indicate that the heater 14 is working.

A control circuit is integrated with the sensor 16 and supplies power to the heater 14 responsive to the sensor 16, for example, with a maximum, time-period limiter.

Alternatively, the control circuitry may include a manually operable switch for an application of a negative pressure. The time-period of the electric current supply to the heater 14 may be pre-set depending on the amount of pre-vapor formulation desired to be vaporized. The control circuitry may be programmable for this purpose. Alternatively, the circuitry may supply power to the heater as long as the sensor 16 detects a pressure drop.

When activated, the heater 14 heats a portion of the wick 28 surrounded by the heater for less than about 10 seconds, more preferably less than about 7 seconds. Thus, the power cycle can range in period from about 2 seconds to about 10 seconds (e.g., about 3 seconds to about 9 seconds, about 4 seconds to about 8 seconds or about 5 seconds to about 7 seconds).

In an embodiment, the pre-vapor formulation supply reservoir 22 includes the pre-vapor formulation storage medium 21 containing pre-vapor formulation material. In FIG. 1, the pre-vapor formulation supply reservoir 22 is contained in an outer annulus between inner tube 62 and outer tube 6 and between stopper 10 and the seal 15. Thus, the pre-vapor formulation supply reservoir 22 at least partially surrounds the central air passage 20 and the heater 14 and the wick 28 extend between portions of the pre-vapor formulation supply reservoir 22.

The pre-vapor formulation storage medium 21 may be a fibrous material comprising cotton, polyethylene, polyester, rayon and/or combinations thereof. The fibers may have a diameter ranging in size from about 6 microns to about 15 microns (e.g., about 8 microns to about 12 microns or about 9 microns to about 11 microns). The pre-vapor formulation storage medium 21 may be a sintered, porous or foamed material. Also, the fibers may be sized to be irrespirable and can have a cross-section which has a y shape, cross shape, clover shape or any other suitable shape.

In another example embodiment, the pre-vapor formulation storage medium 21 may be a tobacco filler or tobacco slurry.

Also, the pre-vapor formulation material has a boiling point suitable for use in the non-combustible smoking device 60. If the boiling point is too high, the heater 14 will not be able to vaporize the pre-vapor formulation in the wick 28. However, if the boiling point is too low, the pre-vapor formulation may vaporize without the heater 14 being activated.

A pre-vapor formulation is a material or combination of materials that may be transformed into a vapor. For example, the pre-vapor formulation may be a liquid, solid and/or gel formulation including, but not limited to, water, beads, solvents, active ingredients, ethanol, plant extracts, natural or artificial flavors, and/or vapor formers such as glycerine and propylene glycol.

The pre-vapor formulation may include a tobacco element including volatile tobacco flavor compounds which are released upon heating. When the tobacco element is in the pre-vapor formulation the physical integrity of the tobacco element is preserved. For example, the tobacco element may be 2-30% by weight in the pre-vapor formulation.

For example, the tobacco element may be in the form of a sheet or shreads and is added after the pre-vapor formulation is added to the pre-vapor formulation storage medium 21.

In operation, with non-combustible smoking device 60 in an assembled configuration, a negative pressure may be applied on the mouth-end insert 8. This negative pressure may cause an internal pressure drop inside non-combustible smoking device 60 that may cause an inlet air flow to enter device 60 via air inlets 44/44'. The internal pressure drop may also cause an internal pressure drop within section 72 as air is drawn through air inlet 44*a* (via an air flow path traveling through section 72). The internal pressure drop formed in section 72 may be sensed by sensor 16. The sensor 16 may then operate to close an electrical circuit that includes the power supply 1. In turn, electrical leads carry an electrical current to heater 14 in order to energize the heater 14. The energized heater 14 in turn heats and vaporizes the pre-vapor formulation material that is drawn toward the heater 14 via the wick 28.

Figure 3:
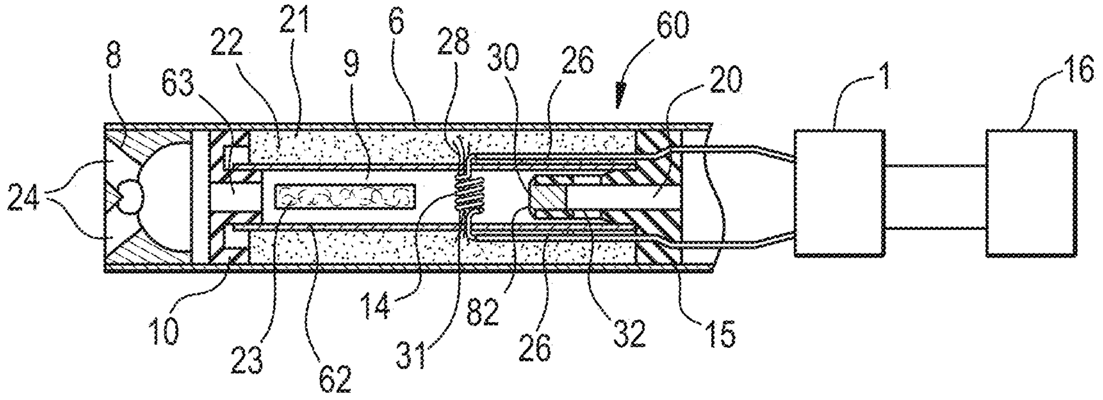
FIG. 3 is a cross-sectional view of an embodiment wherein a non-combustible smoking device includes an air flow diverter, in accordance with an example embodiment.

The pre-vapor formulation material is transferred from the pre-vapor formulation supply reservoir 22 and/or pre-vapor formulation storage medium 21 in proximity of the heater 14 by capillary action in the wick 28. In one embodiment, the wick 28 has a first end portion 29 and a second opposite end portion 31 as shown in FIG. 3. The first end portion 29 and the second end portion 31 extend into opposite sides of the pre-vapor formulation storage medium 21 for contact with pre-vapor formulation material contained therein. The heater 14 at least partially surrounds a central portion of the wick 28 such that when the heater 14 is activated, the pre-vapor formulation in the central portion of the wick 28 is vaporized by the heater 14 to vaporize the pre-vapor formulation material and form the vapor. Due to a negative pressure being applied, the vapor flows from the heater 14, through the tobacco element 23 and out of the mouth-end insert 8.

The vapor may elute tobacco elements into the flow stream. Some thermal reactions may also be present between the vapor and the tobacco element.

One advantage of an embodiment is that the pre-vapor formulation material in the pre-vapor formulation supply reservoir 22 is protected from oxygen (because oxygen cannot generally enter the pre-vapor formulation storage portion via the wick) so that the risk of degradation of the pre-vapor formulation material is significantly reduced. Moreover, in some embodiments in which the outer tube 6 is not clear, the pre-vapor formulation supply reservoir 22 is protected from light so that the risk of degradation of the pre-vapor formulation material is significantly reduced. Thus, a high level of shelf-life and cleanliness can be maintained.

As shown in FIGS. 2A and 2B, the mouth-end insert 8, includes at least two diverging outlets 24 (e.g., 3, 4, 5 or more). The outlets 24 of the mouth-end insert 8 are located at ends of off-axis passages 80 and are angled outwardly in relation to the longitudinal direction of the non-combustible smoking device 60 (i.e., divergently). As used herein, the term “off-axis” denotes at an angle to the longitudinal direction of the non-combustible smoking device 60. Also, the mouth-end insert (or flow guide) 8 may include outlets uniformly distributed around the mouth-end insert 8 so as to substantially uniformly distribute the vapor during use. Thus, the vapor moves in different directions as compared to e-vaping devices having an on-axis single orifice which directs the vapor to a single location.

In addition, the outlets 24 and off-axis passages 80 are arranged such that droplets of unvaporized pre-vapor formulation carried in the vapor impact interior surfaces 81 at mouth-end insert and/or interior surfaces of the off-axis passages such that the droplets are removed or broken apart. In an embodiment, the outlets of the mouth-end insert are located at the ends of the off-axis passages and are angled at 5 to 60 degrees with respect to the central axis of the outer tube 6 so as to more completely distribute vapor during use and to remove droplets.

Preferably, each outlet has a diameter of about 0.015 inch to about 0.090 inch (e.g., about 0.020 inch to about 0.040 inch or about 0.028 inch to about 0.038 inch). The size of the outlets 24 and off-axis passages 80 along with the number of outlets can be selected to adjust the resistance to draw (RTD) of the non-combustible smoking device 60, if desired.

As shown in FIG. 1, an interior surface 81 of the mouth-end insert 8 can comprise a generally domed surface. Alternatively, as shown in FIG. 2B, the interior surface 81' of the mouth-end insert 8 can be generally cylindrical or frustoconical, with a planar end surface. The interior surface is substantially uniform over the surface thereof or symmetrical about the longitudinal axis of the mouth-end insert 8. However, in other embodiments, the interior surface can be irregular and/or have other shapes.

The mouth-end insert 8 is integrally affixed within the tube 6 of the section 70. Moreover, the mouth-end insert 8 may be formed of a polymer selected from the group consisting of low density polyethylene, high density polyethylene, polypropylene, polyvinylchloride, polyetheretherketone (PEEK) and combinations thereof. The mouth-end insert 8 may also be colored if desired.

In an embodiment, the non-combustible smoking device 60 also includes various embodiments of an air flow diverter or air flow diverter means. The air flow diverter is operable to manage air flow at or about around the heater so as to abate a tendency of drawn air to cool the heater, which could otherwise lead to diminished vapor output.

Figure 4:
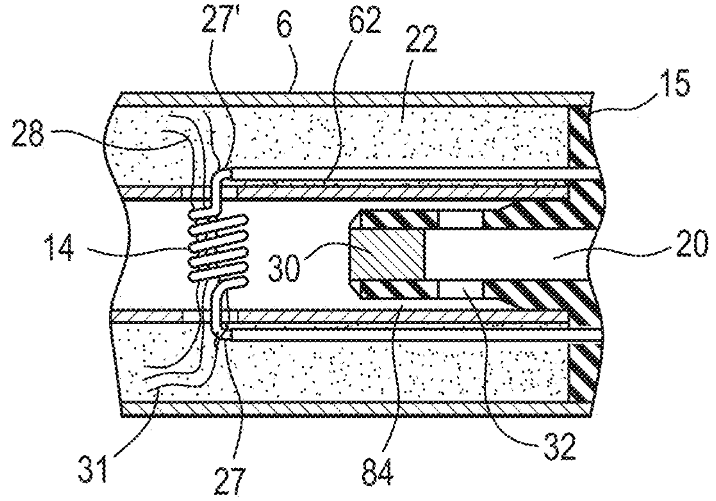
FIG. 4 is an enlarged view of the air flow diverter of the non-combustible smoking device of FIG. 3, in accordance with an example embodiment.

In one embodiment, as shown in FIGS. 3-4, the non-combustible smoking device 60 can include an air flow diverter comprising an impervious plug 30 at a downstream end 82 of the central air passage 20 in seal 15. The central air passage 20 is an axially extending central passage in seal 15 and inner tube 62. The seal 15 seals the upstream end of the annulus between the outer and inner tubes 6, 62. The air flow diverter may include at least one radial air channel 32 directing air from the central air passage 20 outward toward the inner tube 62 and into the outer air passage 9 defined between an outer periphery of a downstream end portion of the seal 15 and the inner wall of inner tube 62.

The diameter of the bore of the central air passage 20 is substantially the same as the diameter of the at least one radial air channel 32. Also, the diameter of the bore of the central air passage 20 and the at least one radial air channel 32 may range from about 1.5 mm to about 3.5 mm (e.g., about 2.0 mm to about 3.0 mm). Optionally, the diameter of the bore of the central air passage 20 and the at least one radial air channel 32 can be adjusted to control the resistance to draw of the non-combustible smoking device 60. In use, the air flows into the bore of the central air passage 20, through the at least one radial air channel 32 and into the outer air passage 9 such that a lesser portion of the air flow is directed at a central portion of the heater 14 so as to reduce or minimize the aforementioned cooling effect of the airflow on the heater 14 during heating cycles. Thus, incoming air is directed away from the center of the heater 14 and the air velocity past the heater is reduced as compared to when the air flows through a central opening in the seal 15 oriented directly in line with a middle portion of the heater 14.

Figure 5:
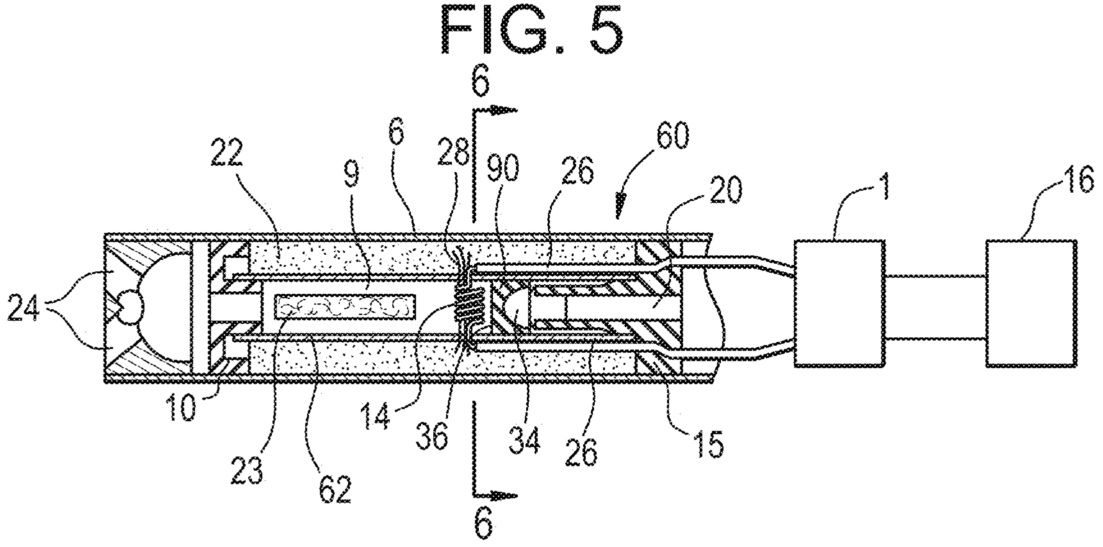
FIG. 5 is a cross-sectional view of an embodiment wherein a non-combustible smoking device includes an air flow diverter, in accordance with an example embodiment.
Figure 6:
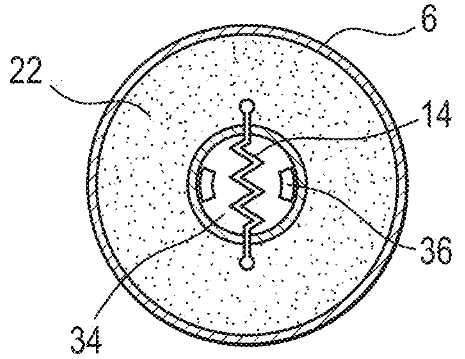
FIG. 6 is a cross-sectional view along line A-A of the non-combustible smoking device of FIG. 6, in accordance with an example embodiment.

In another embodiment, as shown in FIGS. 5-6, the air flow diverter can be in the form of a disc 34 positioned between the downstream end of seal 15 and the heater 14. The disc 34 includes at least one orifice 36 in a transverse wall at a downstream end of an outer tubular wall 90. The at least one orifice 36 may be off-axis so as to direct incoming air outward towards the inner wall of tube 62. During an application of a negative pressure, the disc 34 is operable to divert air flow away from a central portion of the heater 14 so as to counteract the tendency of the airflow to cool the heater as a result of a strong or prolonged negative pressure. Thus, the heater 14 is substantially reduced or prevented from cooling during heating cycles so as to reduce or prevent a drop in the amount of vapor produced during an application of a negative pressure.

Figure 7:
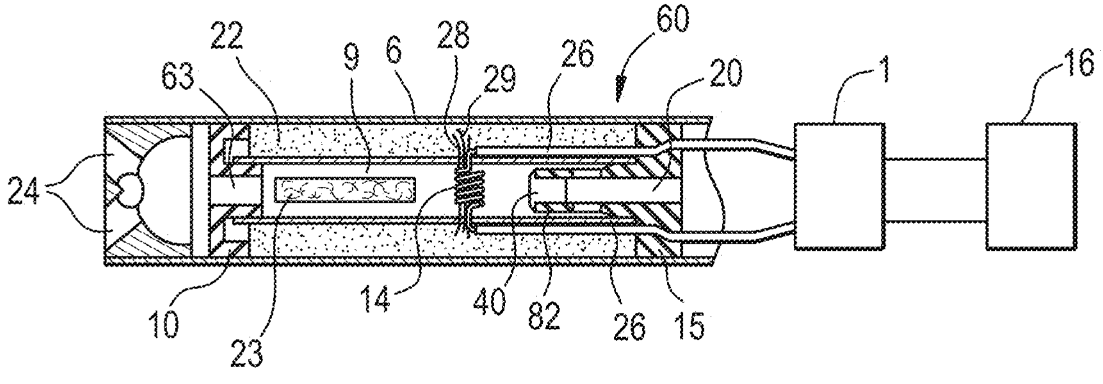
FIG. 7 is a cross-sectional view of an embodiment wherein a non-combustible smoking device includes an air flow diverter, in accordance with an example embodiment.

In yet another embodiment, as shown in FIG. 7, the air flow diverter comprises a frustoconical section 40 extending from the downstream end 82 of a shortened central air passage 20. By shortening the central air passage 20 as compared to other embodiments, the heater 14 is positioned farther away from the central air passage 20 allowing the air flow to decelerate before contacting the heater 14 and lessen the tendency of the air flow to cool the heater 14. Alternatively, the heater 14 can be moved closer to the mouth-end insert 8 and farther away from the central air passage 20 to allow the air flow time and/or space sufficient to decelerate to achieve the same cooling-abatement effect.

The addition of the frustoconical section 40 provides a larger diameter bore size which can decelerate the air flow so that the air velocity at or about the heater 14 is reduced so as to abate the cooling effect of the air on the heater 14 during negative pressure cycles. The diameter of the large (exit) end of the frustoconical section 40 ranges from about 2.0 mm to about 4.0 mm, and preferably about 2.5 mm to about 3.5 mm.

The diameter of the bore of the central air passage 20 and the diameter of the smaller and/or larger end of the frustoconical section 40 can be adjusted to control the resistance to draw of the non-combustible smoking device 60.

The air flow diverter of the various embodiments channels the air flow by controlling the air flow velocity (its speed and/or the direction of the air flow). For example, the air flow diverter can direct air flow in a particular direction and/or control the speed of the air flow. The air flow speed may be controlled by varying the cross sectional area of the air flow route. Air flow through a constricted section increases in speed while air flow through a wider section decreases speed.

The outer tube 6 and/or the inner tube 62 may be formed of any suitable material or combination of materials. Examples of suitable materials include metals, alloys, plastics or composite materials containing one or more of those materials, or thermoplastics that are suitable for food or pharmaceutical applications, for example polypropylene, polyetheretherketone (PEEK), ceramic, and polyethylene. In one embodiment, the material is light and non-brittle.

Figure 8:
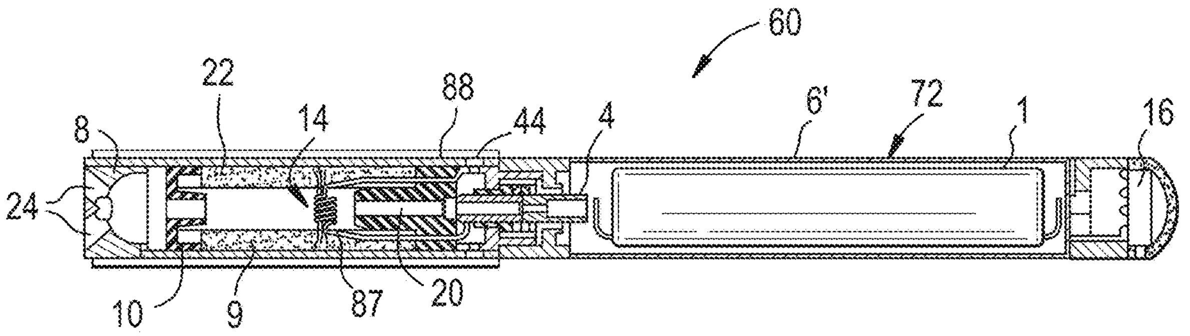
FIG. 8 is a cross-sectional view of a non-combustible smoking device and further including a sleeve assembly, in accordance with an example embodiment.

As shown in FIG. 8, the non-combustible smoking device 60 can also include a sleeve assembly 87 removably and/or rotatably positioned about the outer tube 6 adjacent the first section 70 of the non-combustible smoking device 60. Moreover, the sleeve assembly 87 insulates at least a portion of the first section 70 so as to maintain the temperature of the vapor prior to delivery to the adult vaper. In an embodiment, the sleeve assembly 87 is rotatable about the non-combustible smoking device 60 and includes spaced apart slots 88 arranged transversely about the sleeve assembly such that the slots 88 line up with the air inlets 44 in the first section 70 to allow air to pass into the non-combustible smoking device 60 when a negative pressure is applied on the non-combustible smoking device 60. Before or during vaping, the adult vaper can rotate the sleeve assembly 87 such that the air inlets 44 are at least partially blocked by the sleeve assembly 87 so as to adjust the resistance to draw and/or ventilation of the non-combustible smoking device 60.

The sleeve assembly 87 is made of silicone or other pliable material so as to provide a soft mouthfeel to the adult vaper. However, the sleeve assembly 87 may be formed in one or more pieces and can be formed of a variety of materials including plastics, metals and combinations thereof. In an embodiment, the sleeve assembly 87 is a single piece formed of silicone. The sleeve assembly 87 may be removed and reused with other non-combustible smoking devices or can be discarded along with the first section 70. The sleeve assembly 87 may be any suitable color and/or can include graphics or other indicia.

Figure 9:
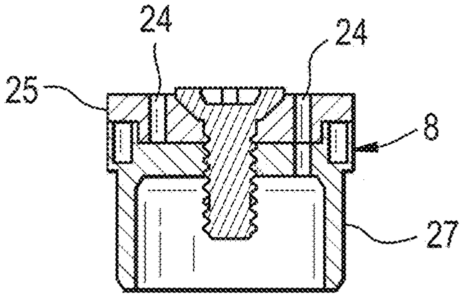
FIG. 9 is a cross-sectional view of a second embodiment of a mouth-end insert for use with a non-combustible smoking device, in accordance with an example embodiment.
Figure 10:
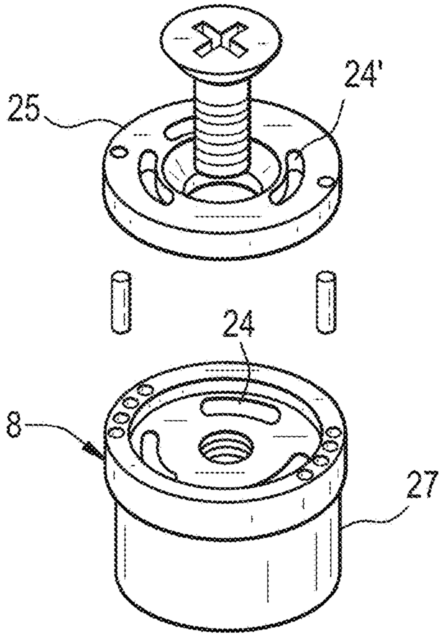
FIG. 10 is an exploded view of the mouth-end insert of FIG. 9, in accordance with an example embodiment.

As shown in FIGS. 9-10, in an alternative embodiment, the non-combustible smoking device can include a mouth-end insert 8 having a stationary piece 27 and a rotatable piece 25. Outlets 24, 24' are located in each of the stationary piece 27 and the rotatable piece 25. One or more of the outlets 24, 24' align as shown to allow vapor to enter an adult vaper's mouth. However, the rotatable piece 25 can be rotated within the mouth-end insert 8 so as to at least partially block one or more of the outlets 24 in the stationary piece 27. Thus, the amount of vapor output may be varied with each application of a negative pressure. The outlets 24, 24' can be formed in the mouth-end insert 8 such that the outlets 24, 24' diverge.

In another embodiment, the air flow diverter comprises the addition of a second wick element adjacent to but just upstream of the heater 14. The second wick element diverts portions of the air flow about the heater 14.

While FIGS. 1, 3, 5 and 7-8 illustrate a tobacco element in an outer air passage, example embodiments are not limited thereto.

Figure 11A:
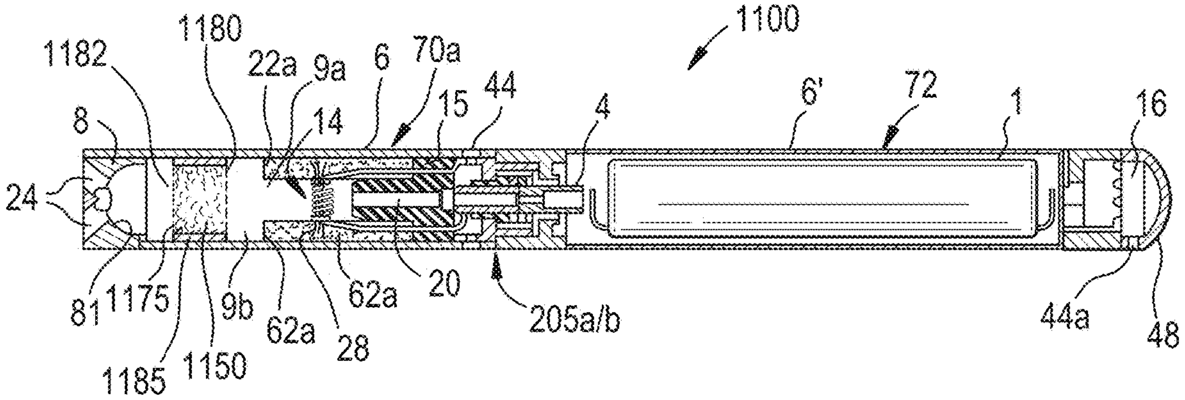
FIGS. 11A-11B illustrate example embodiments of a non-combustible smoking device including a tobacco element.

FIG. 11A illustrates an example embodiment of a non-combustible smoking device 1100 including a tobacco element 1150. The non-combustible smoking device 1100 is similar to the non-combustible smoking device 60. Thus, for the sake of brevity, only the differences will be described.

The non-combustible smoking device 1100 includes a pre-vapor formulation supply reservoir 22*a*. The pre-vapor formulation supply reservoir 22*a* is the same as the pre-vapor formulation supply reservoir 22 except the pre-vapor formulation supply reservoir 22*a* is shorter in the longitudinal direction.

A first section 70*a* includes the outer tube 6 (or housing) extending in a longitudinal direction and an inner tube 62*a* coaxially positioned within the outer tube or housing 6. The inner tube 62*a* defines a first outer air passage 9*a*. The first outer air passage 9*a* opens to a second outer air passage 9*b*.

An end of the inner tube 62*a* and the mouth-end insert 8 defines the second outer air passage 9*b*. In other words, the outer tube 6 may define a diameter in the latitudinal direction of the second outer air passage 9*b*. As shown, the diameter in the latitudinal direction of the second outer air passage 9*b* is larger than a diameter in the latitudinal direction of the first outer air passage 9*a*.

Within the second outer air passage 9*b* is the tobacco element 1150. The tobacco element 1150 may be inserted into the second outer air passage 9*b* by removing the mouth-end insert 8 and inserting the tobacco element 1150 into the second outer air passage 9*b*, for example.

The tobacco element 1150 may be a tobacco plug which refers to a compressed form of tobacco including, but not limited to tobacco strands, rolled tobacco or filler. The tobacco plug may be wrapped in natural tobacco, reconstituted sheet tobacco or aluminum, for example. While only one tobacco plug is illustrated, it should be understood that a plurality of tobacco plugs may be used. Fibrous segments (e.g., cellulose acetate, other synthetic fibers, or natural fibers) may be placed between the plurality of tobacco plugs.

For example, a cylindrical housing 1185 holds tobacco. The cylindrical housing 1185 may be made of aluminum, for example. The cylindrical housing 1185 has an outer diameter that fits with the diameter of the outer air passage 9*b*. Along the longitudinal axis of the housing 6, mesh screens 1175 and 1180 fit at ends of the cylindrical housing 1185 to enclose the tobacco in the cylindrical housing 1185. As shown in FIG. 11A, the mesh screens 1175 and 1180 include openings 1182 to allow air to pass from one end of the cylindrical housing through the tobacco and out of the end of the cylindrical housing 1185 closest to the mouth-end insert 8.

The tobacco element 1150 is arranged in such a way to allow the vapor generated by the heater 14 to pass through the tobacco. For example, the tobacco element 1150 may be spaced a first distance from the mouth-end insert 8 and a second distance from the pre-vapor formulation supply reservoir 22. The first distance and the second distance may be the same or different.

Due to a negative pressure being applied, the vapor flows from the heater 14, through the tobacco element 1150 and out of the mouth-end insert 8. The heater 14 may be a set distance from the tobacco element 1150 or contacting the tobacco element 1150 such that the heater 14 heats the tobacco to a temperature (as described above) during an application of a negative pressure. In an example, the heater 14 may be 1-5 mm from the tobacco element 1150.

Figure 11B:
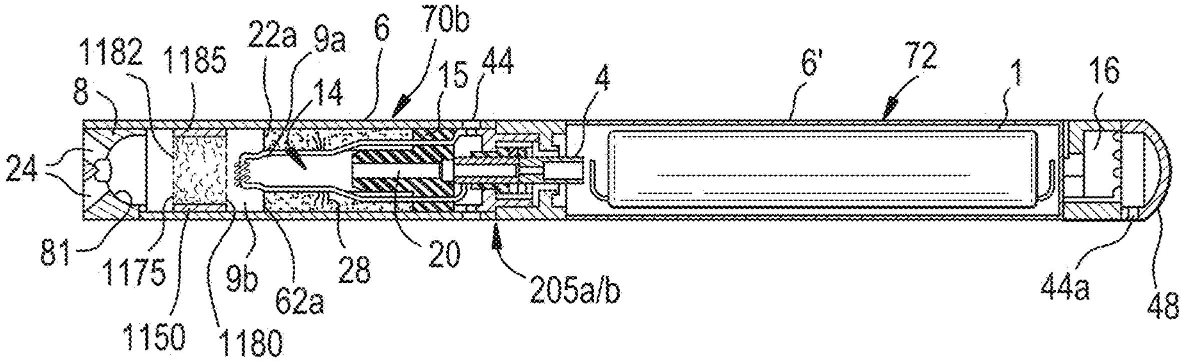

While the inner tube 62*a* is shown as extending past the heater 14 in the longitudinal direction to the mouth-end insert 8, it should be understood that the heater 14 may be arranged to extend into the second outer air passage 9*b*. As a result, the tobacco element 1150 may be spaced apart from the heater 14 or in contact with the heater 14, such as shown FIG. 11B. In FIG. 11B, the heater 14 is in the second outer passage 9*b* of a section 70*b*. Thus, pre-vapor formulation supply reservoir 11*a*, the heater 14 and the tobacco element 1150 are sequentially arranged.

While the gasket 10 is not illustrated, the non-combustible smoking device 11 may include the gasket 10.

Figure 12:
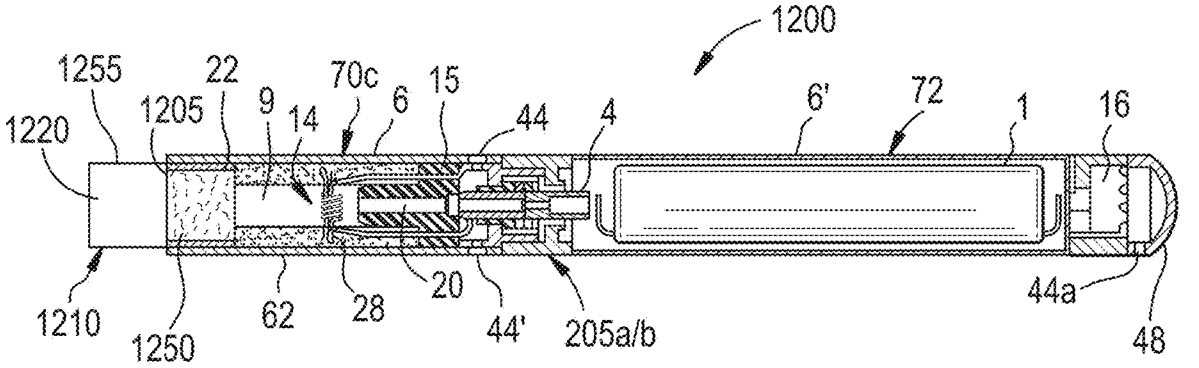
FIG. 12 illustrates an example embodiment of a non-combustible smoking device.

FIG. 12 illustrates an example embodiment of a non-combustible smoking device 1200. FIG. 12 illustrates an example embodiment of a non-combustible smoking device 1200 including a tobacco element 1250. The non-combustible smoking device 1200 is similar to the non-combustible smoking device 60 except a section 70*c* does not include the mouth-end insert 8, the tobacco element 23 and the gasket 10 and the non-combustible smoking device 1200 further includes an insert 1210. Thus, for the sake of brevity, only the differences will be described.

By removing the mouth-end insert 8 and the gasket 10, the non-combustible smoking device 1200 includes a receiving area 1205 fitted to receive a tobacco insert 1210. The receiving area 1205 is defined by the outer tube 6 and an end of the pre-vapor formulation supply reservoir 22.

The tobacco insert 1210 may be a cigarette or cigar. For example, the tobacco insert may be a filtered cigarette, a non-filtered cigarette, a cigarillo, a filter tipped cigar filter, a tipped cigar or an untipped cigar/cigarillo, for example. However, example embodiments are not limited thereto.

The tobacco insert 1210 is a detachable insert. In the example shown in FIG. 12, the tobacco insert 1210 may be a cigarette or a portion of a cigarette. The tobacco insert 1210 includes a filter 1220 and a tobacco element 1250. In example embodiments where the tobacco insert is an untipped cigar/cigarillo, the tobacco insert does not include a filter.

Tipping paper 1255 may overlap the filter 1220 and the tobacco element 1250. The tipping paper 1255 may cover surface areas of the tobacco insert 1210 that extend in along the outer tube 6. Thus, the tipping paper 1255 provides stiffness to the tobacco insert 1210, permitting easier insertion to the receiving area 1205. An aluminum foil may also be used to contain the tobacco element 1250, with or without additional tipping paper.

The position of the heater 14 is not limited to the position shown in FIG. 12A. For example, the heater 14 may be positioned at the end of the outer air passage 9 such that the heater 14 is closer to the tobacco element 1250 and/or in contact with the tobacco element 1250. In another example embodiment, the heater 14 may protrude out of the outer air passage 9 in the same manner as shown in FIG. 11B.

The heater 14 may be a set distance from the tobacco element 1250 or contacting the tobacco element 1250 such that the heater 14 heats the tobacco element 1250 to a temperature (as described above) during an application of a negative pressure.

In operation, with non-combustible smoking device 1200 in an assembled configuration, a negative pressure may be applied on the tobacco insert 1210. The negative pressure may cause an internal pressure drop inside non-combustible smoking device 1200 that may cause an inlet air flow to enter the device 1200 via air inlets 44/44'. The internal pressure drop may also cause an internal pressure drop within section 72 as air is drawn through air inlet 44*a* (via an air flow path traveling through section 72). The internal pressure drop formed in section 72 may be sensed by sensor 16. The sensor 16 may then operate to close an electrical circuit that includes the power supply 1. In turn, electrical leads carry an electrical current to heater 14 in order to energize the heater 14. The energized heater 14 in turn heats and vaporizes a portion of the pre-vapor formulation that is drawn toward the heater 14 via the wick 28.

Pre-vapor formulation material is transferred from the pre-vapor formulation supply reservoir 22 and/or pre-vapor formulation storage medium 21 in proximity of the heater 14 by capillary action in the wick 28. When the heater 14 is activated, the pre-vapor formulation in the central portion of the wick 28 is vaporized by the heater 14 to vaporize the pre-vapor formulation material and form vapor. Due to a negative pressure being applied, the vapor flows from the heater 14, through the tobacco element 1250 and out of the filter 1220.

In the example shown in FIG. 12, the filter 1220 may be a cellulose acetate (CA) filter. CA filter elements, such as triacetin, can be eluted into vapor. Vapor phase nicotine and other volatile elements in vapor can be reduced by a presence of tobacco.

Figure 13A:
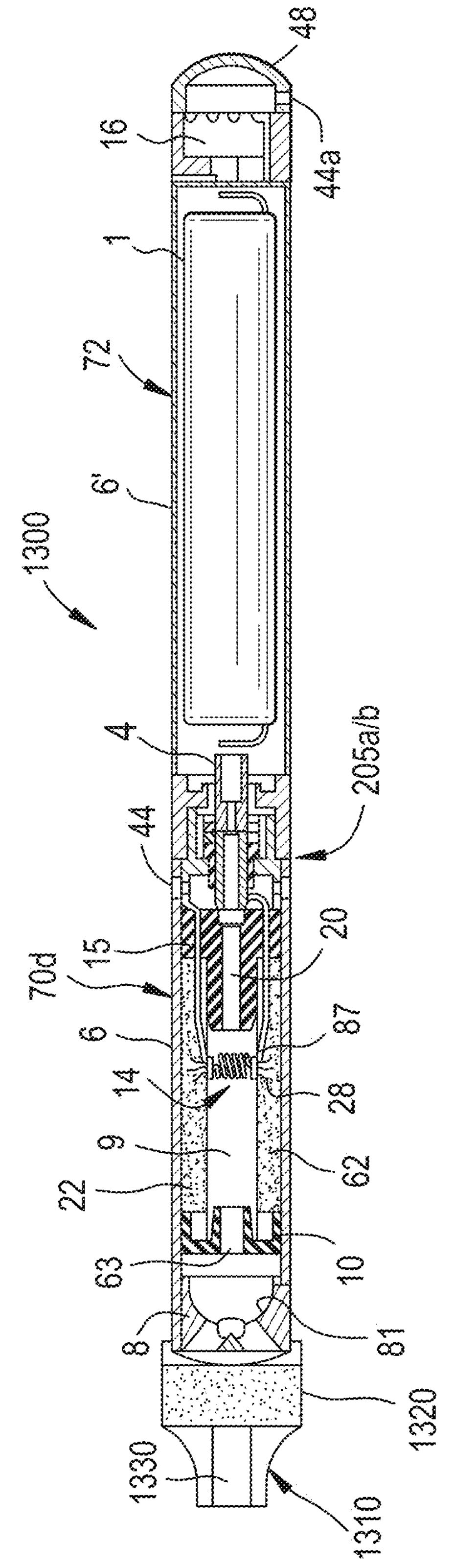
FIGS. 13A-13B illustrate example embodiments of a non-combustible smoking device including a tobacco element.

FIG. 13A illustrates an example embodiment of a non-combustible smoking device 1300.

The non-combustible smoking device 1300 is similar to the non-combustible smoking device 60 except a section 70*d* does not include the tobacco element 23 and the non-combustible smoking device 1300 further includes a detachable mouthpiece 1310. Thus, for the sake of brevity, only the differences will be described.

The detachable mouthpiece 1310 includes a tobacco element 1320. The tobacco element 1320 may be contained in a plug or bag, and attached to the inside of mouthpiece 1310. The detachable mouthpiece 1310 fits over a portion the outer tube 6 to form a seal between the detachable mouthpiece and the section 70*d*. The detachable mouthpiece 1310 may form the seal by sliding onto the outer tube 6 or having a connection mechanism (e.g., male/female) to connect to the outer tube 6.

In operation, with non-combustible smoking device 1300 in an assembled configuration, a negative pressure may be applied on the detachable mouthpiece 1310. Due to a negative pressure being applied, the vapor flows from the heater 14, through the mouth-end insert 8, into the tobacco element 1320 and out of the detachable mouthpiece 1310 through an air passage 1330.

The heater 14 may be a set distance from the tobacco element 1320 or contacting the tobacco element 1320 such that the heater 14 heats the tobacco element 1320 to a temperature (as described above) during an application of a negative pressure.

Figure 13B:
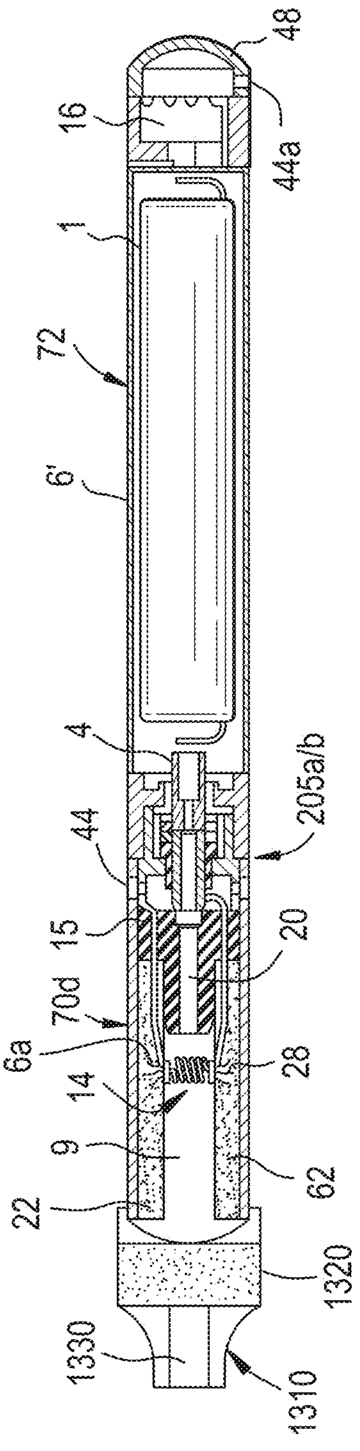

In another example embodiment, the mouth-end insert 8 and the gasket 10 may be omitted such as shown in FIG. 13B. In the embodiment shown in FIG. 13B, a tube 6*a* is shorter than the tube 6, of FIG. 13A.

In other example embodiments, the tobacco element may be in the pre-vapor formulation supply reservoir and/or function as the pre-vapor formulation storage medium.

Figure 14B:
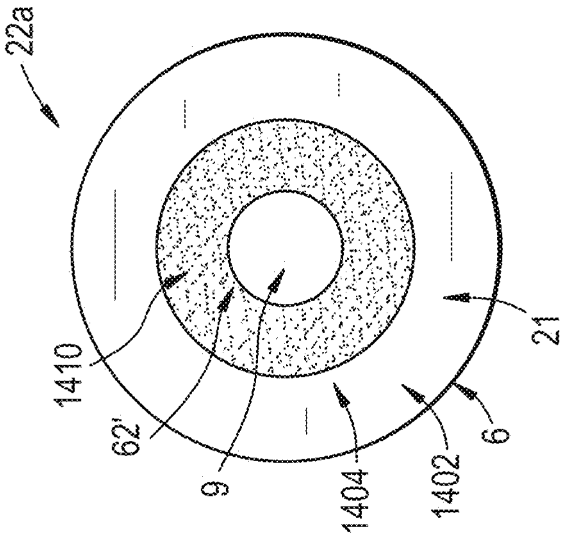
FIGS. 14A-B illustrate an example embodiment of a pre-vapor formulation supply reservoir.
Figure 14A:
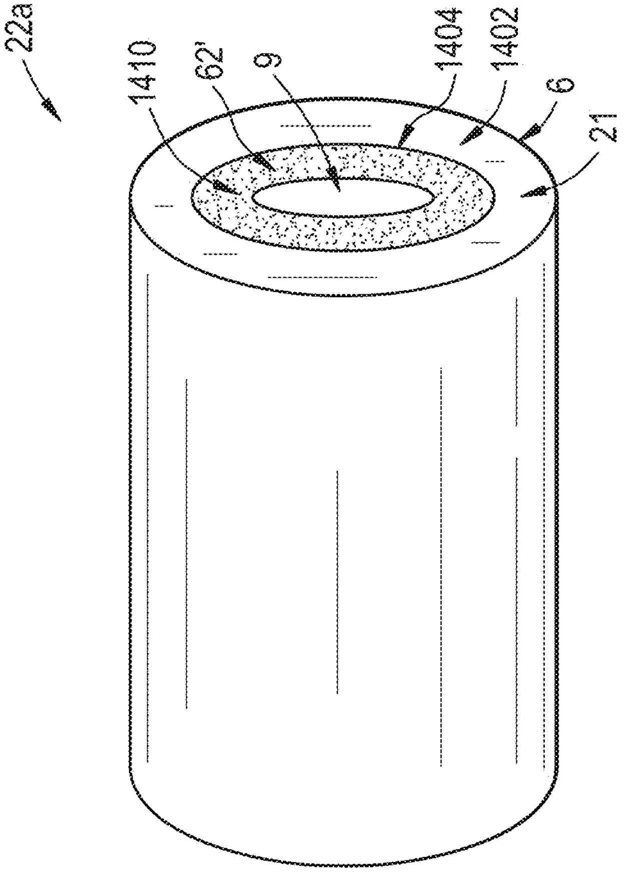

For example, FIGS. 14A-B illustrate an example embodiment of a pre-vapor formulation supply reservoir. A pre-vapor formulation supply reservoir 22*a* may be used as the pre-vapor formulation supply reservoir 22.

As shown, the pre-vapor formulation supply reservoir 22*a* includes a pre-vapor formulation 1402, an intermediate tube 1404, a tobacco element 1410 and an inner tube 62'. The inner tube 62' defines the air passage 9 and may include a metal grid, screen or mesh, for example.

In another example embodiment, the inner tube 62' may be the inner tube 62 may be formed of any suitable material or combination of materials. Examples of suitable materials include metals, alloys, plastics or composite materials containing one or more of those materials, or thermoplastics that are suitable for food or pharmaceutical applications, for example polypropylene, polyetheretherketone (PEEK), ceramic, and polyethylene.

The intermediate tube 1404 may include a glass fiber. The pre-vapor formulation 1402 is between the intermediate tube 1404 and the outer tube 6 and may be in the pre-vapor formulation storage medium 21.

The tobacco element 1410 is between the inner tube 62' and the intermediate tube 1404. The tobacco element 1410 may be tobacco sheet, shreds, powder, beads or a sponge, for example. The inner tube 62' may include extenders protruding into the tobacco to help heat transfer.

In operation, a negative pressure may be applied to the non-combustible smoking device, which activates the heater 14, as described above. The heater heats the pre-vapor formulation 1402 to form a vapor and the vapor flows from the heater 14, through the tobacco element 1410 and into the air passage 9.

As a result, the tobacco element 1410 is exposed to heat from the vapor and from the heater 14. Therefore, a tobacco aroma is imparted on the vapor.

In an example embodiment, an amount of tobacco element (e.g., filler) in the non-combustible smoking device may produce about a same number of applications of a negative pressure as a cigarette. Alternatively, the amount of tobacco element may produce a fixed number of applications of a negative pressure.

In an example embodiment, the tobacco element may have nicotine removed.

Example embodiments described in FIGS. 1-14B may be combined to utilize a tobacco element in more than one location. For example, a first tobacco element can be combined with the pre-vapor formulation in the pre-vapor formulation supply reservoir and a second tobacco element may be in the passage 9. In other example embodiment, a first tobacco element can be combined with the pre-vapor formulation in the pre-vapor formulation supply reservoir and a second tobacco element may be a tobacco plug in the second outer air passage 9*b*. In another example embodiment, a first tobacco element can be combined with the pre-vapor formulation in the pre-vapor formulation supply reservoir and a second tobacco element may be in an insert or detachable mouthpiece. In another example embodiment, a first tobacco element can be in the passage 9 and a second tobacco element may be in an insert or detachable mouthpiece.

Example embodiments provide a non-combustible smoking device having a heater that heats a pre-vapor formulation and may provide heat to a tobacco element. More specifically, the non-combustible smoke device according to example embodiments exposes a vapor to a tobacco element and/or exposes a pre-vapor formulation to a tobacco element. When the tobacco element is in the pre-vapor formulation the physical integrity of the tobacco element is preserved.

In other example embodiments, a non-combustible smoke device can be a pod device or tank device that exposes a vapor to a tobacco element and/or exposes a pre-vapor formulation to a tobacco element.

While a single heater is described with reference to FIGS. 1-14B, example embodiments may include a multiple heater non-combustible smoking device. A first heater may be the heater 14 to vaporize the pre-vapor formulation and a second heater may be used to heat the tobacco element. The second heater may penetrate the tobacco element.

Figure 15A:
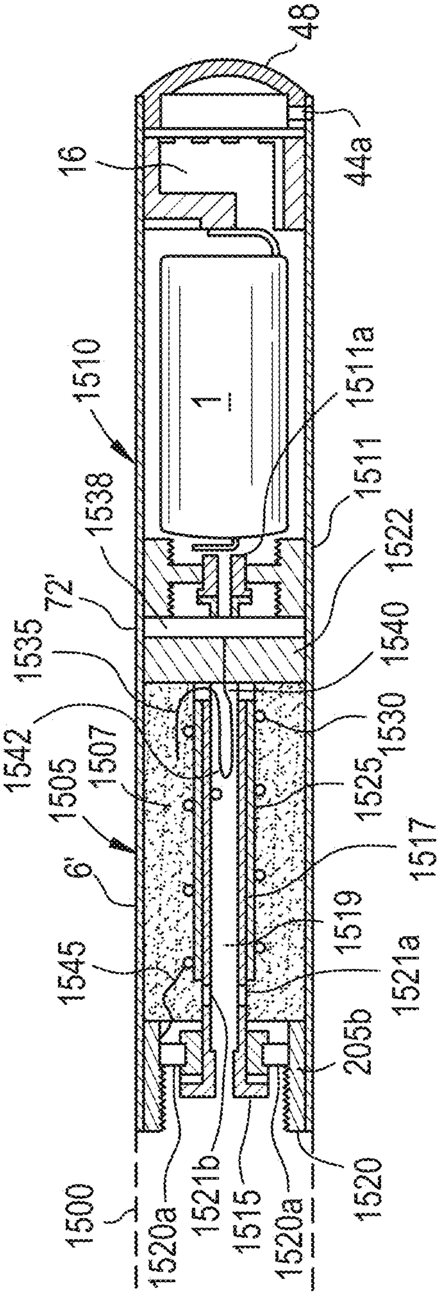
FIGS. 15A-B illustrates an example embodiment of a non-combustible smoking device having a plurality heaters.
Figure 15B:
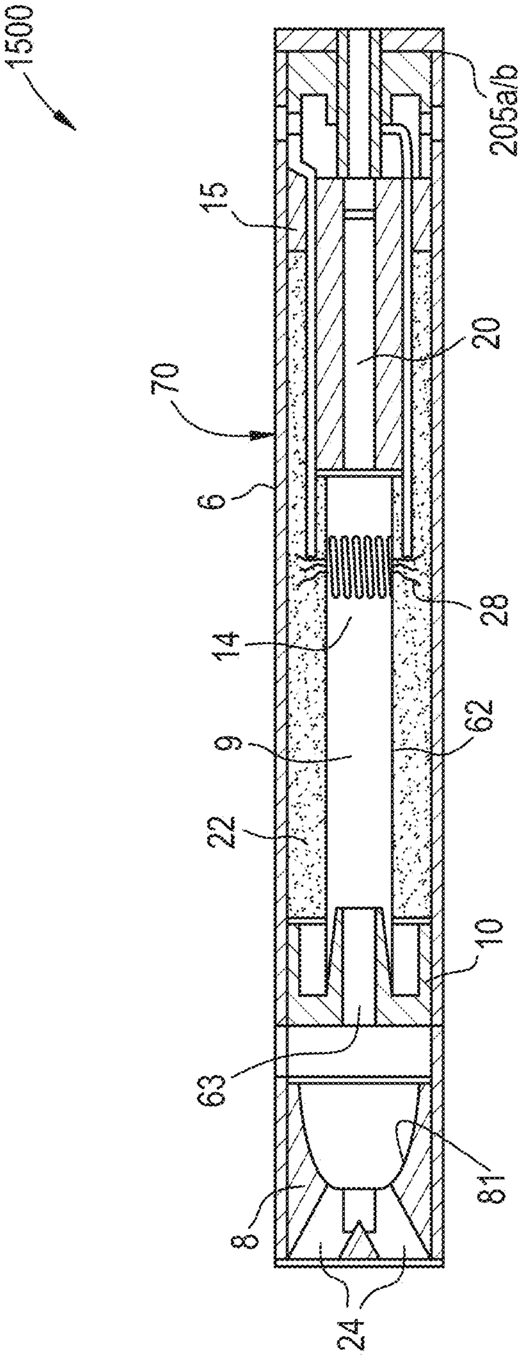

For example, FIGS. 15A-15B illustrates an example embodiment of a non-combustible smoking device having a plurality heaters.

In FIG. 15A, a first section 1500 may be similar to the first section 70, shown in FIG. 1, without the tobacco element 23. FIG. 15B illustrates the first section 1500. Since the first section 1500 is the same as the first section 70 without the tobacco element 23, for sake of brevity, the first section 1500 is not described in further detail.

As shown in FIG. 15A, a second section 72' of the non-combustible smoking device includes a tobacco housing 1505 and a power housing 1510. The tobacco housing 1505 and the power housing 1510 may be separate cartridges that are connected together by a connecting portion 1511. The connecting portion 1511 may be the same as the threaded connection 205.

The tobacco housing 1505 houses tobacco 1507 and is configured to allow an aroma from the tobacco 1507 to flow into the first section 1500.

The tobacco housing includes the connector 205*b*, which has an anode portion 1515 and a cathode portion 1520. The anode portion 1515 includes an annular section 1517 that extends longitudinally in the tobacco housing 1505. The anode portion 1515 includes two holes 1521*a* and 1521*b* to allow air to flow into the tobacco 1507 and a channel 1519 when a negative pressure is applied on the mouth-end insert 8. Both the anode portion 1515 and the cathode portion 1520 include an electrically conductive material such as plated brass or stainless steel. The channel 1519 is defined in part by the anode portion 1515 in the longitudinal direction. A filter 1522 is located at one end of the channel 1519 and another end of the channel 1519 is open to the first section 1500. The filter 1522 may include cellulous acetate, glass fiber, ceramic, cotton, or any chemically inert porous material. As a result, the channel 1519 provides a path for air to flow into the tobacco 1507.

A fibrous sleeve 1525 covers at least a portion of the annular portion 1517 of the anode portion 1515. The fibrous sleeve 1525 may be a cellulosic material or polyethylene terephthalate and may extend from ends of the holes 1521*a,* 1521*b* to the filter 1522. The fibrous sleeve 1525 aids in controlling the temperature by absorbing heat emitted from a coiled heater 1530. The fibrous sleeve 1525 may be fiber glass or any material that is chemically inert and not electrically conductive. The fibrous sleeve 1525 electrically separates the heater 1530 and the anode portion 1515.

A coiled heater 1530 wraps around the fibrous sleeve 1525 in the longitudinal direction and heats the tobacco when power is supplied to the heater 1530 from the power supply 1. The heater 1530 may heat the tobacco and not burn it. For example, the heater 1530 may operate at around 190° C. or could be varied based on a power supply control. The heater 1530 heats the tobacco 1507 to generate a tobacco aroma.

To receive power from the power supply 1, the heater 1530 is attached to the anode portion 1515 and the cathode portion 1520. More specifically, an anode of the power supply 1 is connected to an anode portion 1511*a* of the connecting portion 1511 which is connected to a battery connector 1538. The anode portion 1515 is connected to the battery connector by a wire 1540. While the wire 1540 is illustrated as passing through the filter 1540, the wire may pass between the filter 1540 and the outer tube 6'. The heater 1530 is connected to the anode portion 1515 by a wire 1535. The wire 1540 and 1535 form a soldered connection 1542 on the anode portion 1515.

In addition, the heater 1530 is soldered to wire 1545 which is connected to the cathode portion 1520. The wire 1545 may be connected to the cathode portion 1520 by, for example, spot welding or soldering the two electrical leads of the heater 252. It should be understood that connections should not be limited to soldering or spot welding. Where soldering is used welding may be used instead and vice versa.

Figure 16:
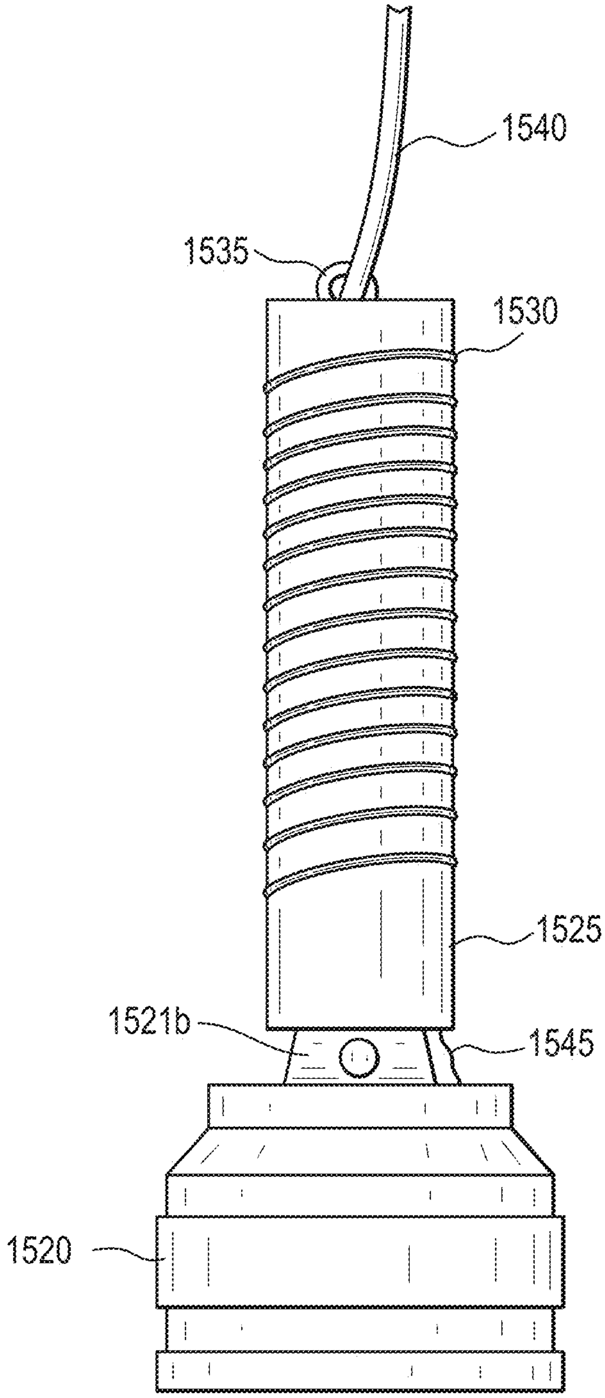
FIG. 16 illustrates a top view of a coiled heater shown in FIG. 15A.

FIG. 16 illustrates a top view of the coiled heater 1530 surrounding the fibrous sleeve 1525. As shown, the coiled heater 1530 wraps around the fibrous sleeve 1525. The wire 1540 extends from the annular section 1517 of the anode portion 1515 past the fibrous sleeve 1525 to the battery connector 1538. Moreover, the sleeve 1525 extends to the hole 1521*b* of the anode portion 1515.

Referring back to FIG. 15A, the cathode portion 1520 includes holes 1520*a*.

Figure 17:
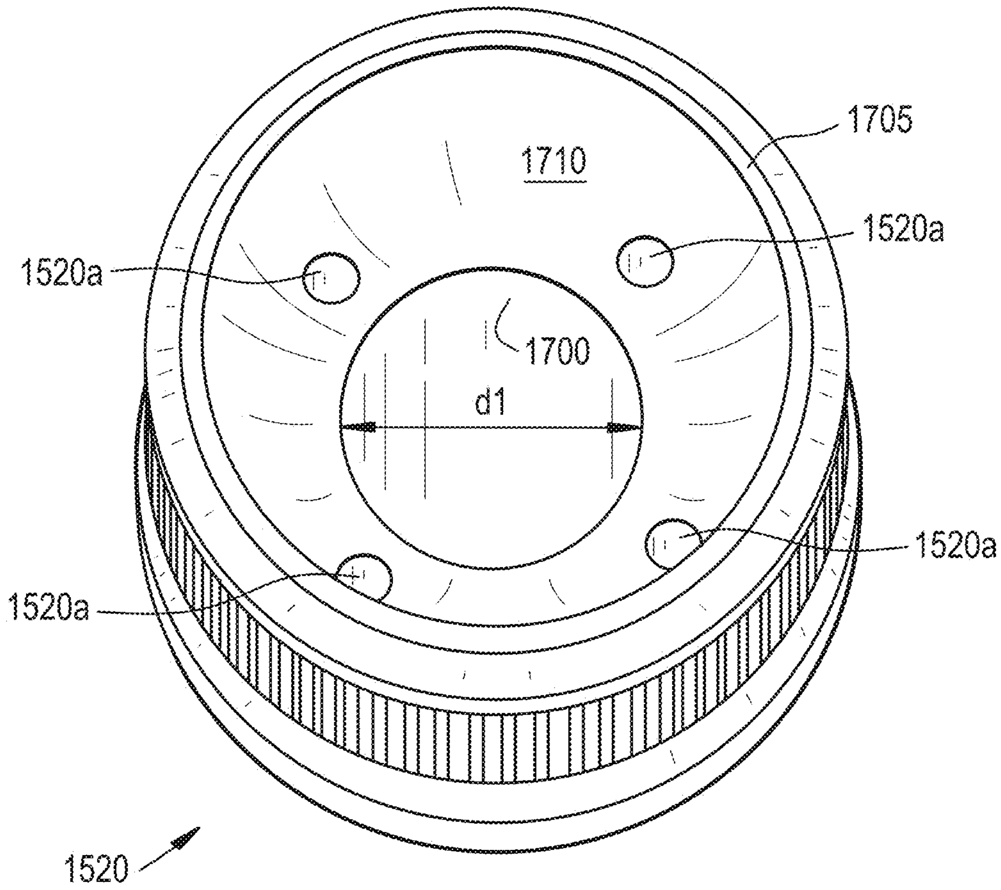
FIG. 17 illustrates a top view of a cathode portion shown in FIG. 15A.

FIG. 17 illustrates a top view of the cathode portion 1520, according to an example embodiment. As shown, the cathode portion 1520 includes four holes 1520*a*. While four holes 1520*a* are illustrated, it should be understood that greater than or less than four holes may be used. Moreover, an inner surface 1700 has a diameter d1 that defines a receiving area for the anode portion.

The cathode portion 1520 includes an upper circular area 1705 and a lower circular area 1710. The holes 1520*a* are spaced approximately 90 degrees from each other and extend through the lower circular area 1710 to provide airways between the tobacco housing 1505 and the first section 1500.

More specifically, when a negative pressure is applied on the mouth-end insert 8, air flows through the channel 1519 as well as through the tobacco 1507 and the holes 1520*a*. The air flowing through the channel 1519 into the section 1500 will also have tobacco aroma due to the air flow path provided by the holes 1521*a* and 1521*b* in the anode portion 1515.

Figure 18:
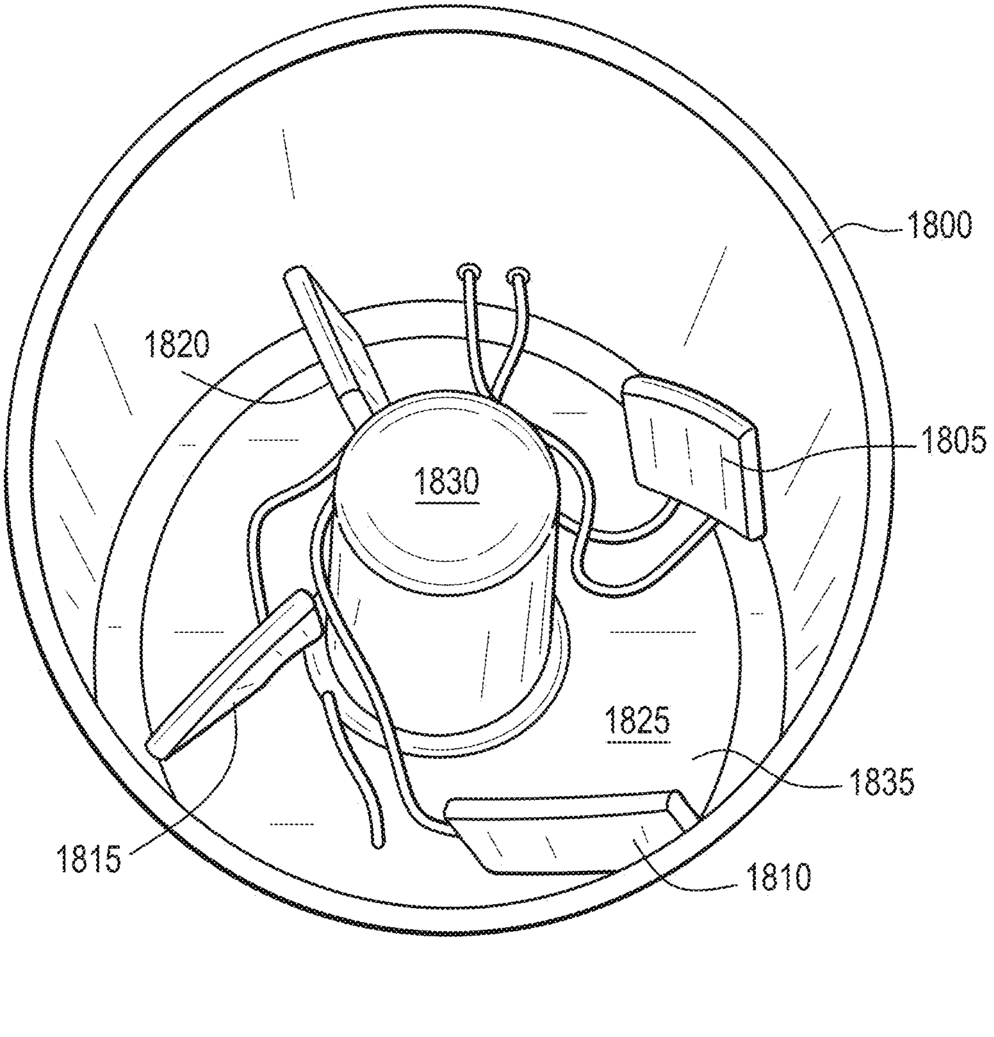
FIG. 18 illustrates a tobacco housing for a non-combustible smoking device according to an example embodiment.

FIG. 18 illustrates a tobacco housing for a non-combustible smoking device according to an example embodiment. As shown in FIG. 18, a tobacco housing 1800 includes a tobacco receiving area 1825 and a protrusion 1830 extending from a surface 1835 of the tobacco receiving area 1825. The tobacco housing 1800 is cylindrical in shape and holds tobacco to be heated from heaters 1805, 1810, 1815 and 1820. The heaters 1805, 1810, 1815 and 1820 extend from the protrusion 1830 into the receiving area 1825. The tobacco housing 1800 may be upstream of a vapor generating area. Thus, the heaters 1805, 1810, 1815 and 1820 heat the tobacco to provide an aroma to the vapor generated downstream. The heaters 1805, 1810, 1815 and 1820 are connected to a power source such as the power supply 1.

Figure 19:
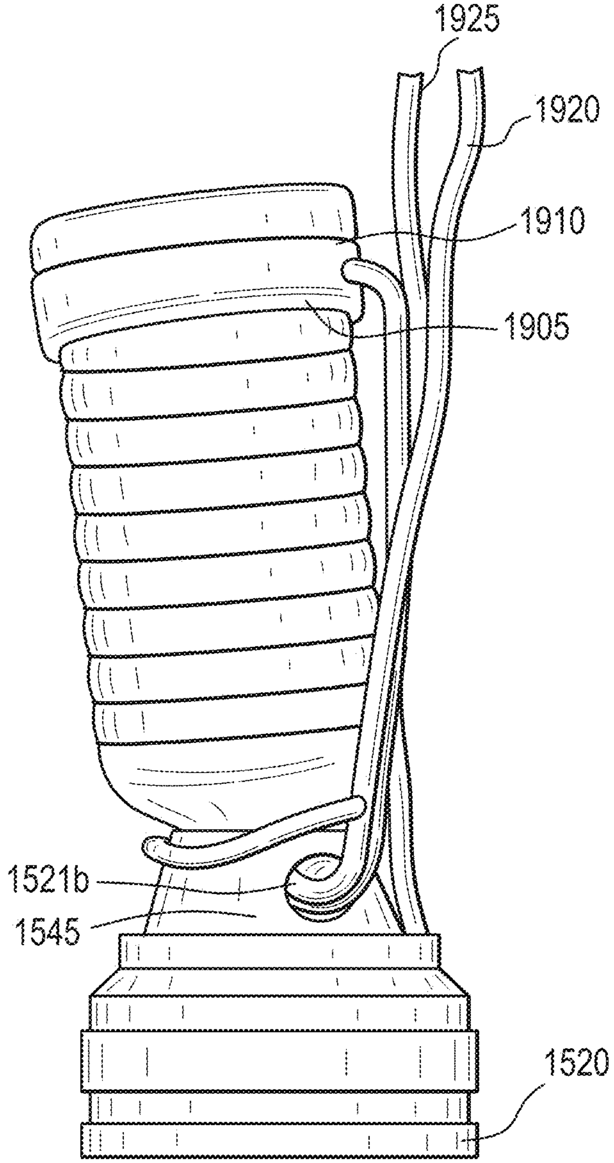
FIG. 19 illustrates another example embodiment of a non-combustible smoking device having a plurality heaters.

FIG. 19 illustrates another example embodiment of a non-combustible smoking device having a plurality heaters.

FIG. 19 illustrates a mesh heater 1905 covered in a fiber glass shield 1910 to help control the temperature. Tobacco is between the mesh heater 1905 and the fiber glass shield 1910. The mesh heater 1905 and fiber glass shield 1910 may be used instead of the tobacco heating arrangement illustrated in FIG. 15A. Thus, the fiber glass shield 1910 may abut the housing 6. The mesh heater 1905 is connected to the power supply 1 through anode and cathode wires 1920 and 1925. The mesh is coiled from the top to the bottom of the cartridge.

The non-combustible smoking devices according to example embodiments may be stored in various configurations.

Figure 20:
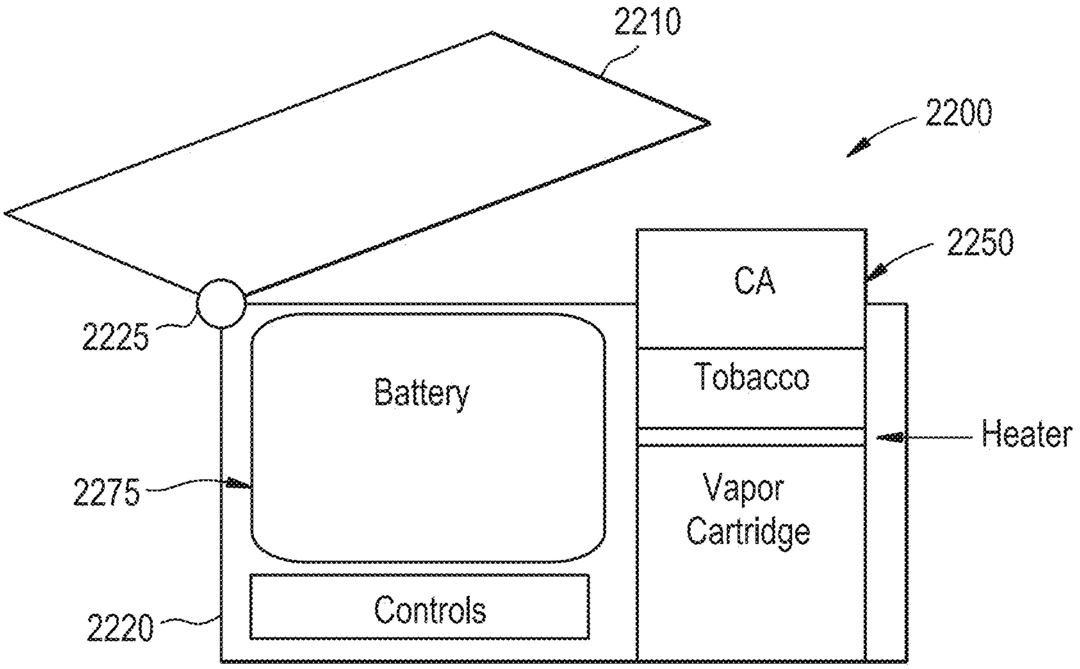
FIG. 20 illustrates a flip top container for a non-combustible smoking device according to an example embodiment.

FIG. 20 illustrates a flip top container for a non-combustible smoking device according to an example embodiment.

As shown, a flip top container 2200 includes a top 2210 and a bottom receiving portion 2220. The bottom receiving portion 2220 is arranged in a fashion such that a first section 2250 of a non-combustible smoking device and a second section 2275 of the non-combustible smoking device are arranged side-by-side. For example, the first section 2250 may be the section 70*c* and the second section 2275 may be the section 72. The top portion 2210 may pivot about a hinge 2225, allowing an adult vaper to open and close the flip top container 2200.

Figure 21:
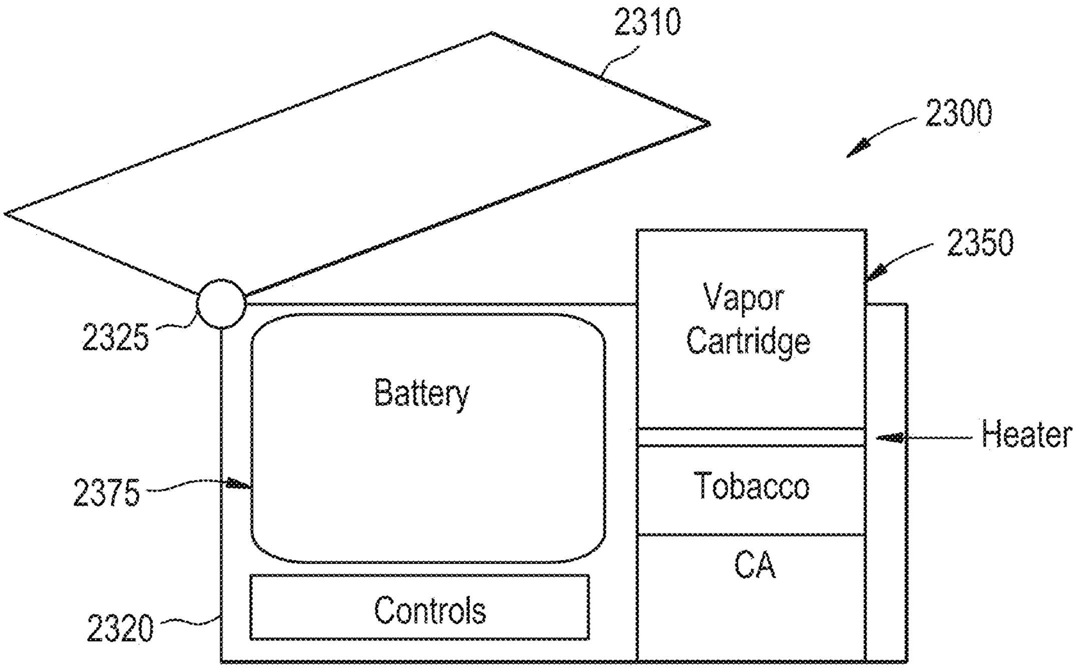
FIG. 21 illustrates a flip top container for a non-combustible smoking device according to another example embodiment.

FIG. 21 illustrates a flip top container for a non-combustible smoking device according to another example embodiment.

As shown, a flip top container 2300 includes a top 2310 and a bottom receiving portion 2320. The bottom receiving portion 2320 is arranged in a fashion such that a first section 2350 of a non-combustible smoking device and a second section 2375 of the non-combustible smoking device are arranged side-by-side. For example, the first section 2350 may be the section 70*c* and the second section 2375 may be the section 72. The top portion 2310 may pivot about a hinge 2325, allowing an adult vaper to open and close the flip top container 2300.

In other example embodiments, a non-combustible smoking device includes an inductive heater where a coil is outside of the tobacco and a reactive element is on a surface of the tobacco.

In other example embodiments, a temperature controller may be required to prevent over heating of the tobacco and prevent burning of the tobacco.

By utilizing a plurality of heaters, a coil heater and/or a mesh heater, the surface area of tobacco exposed to heat increases thereby generating a larger amount of vapor to an adult vaper.

Figure 22:
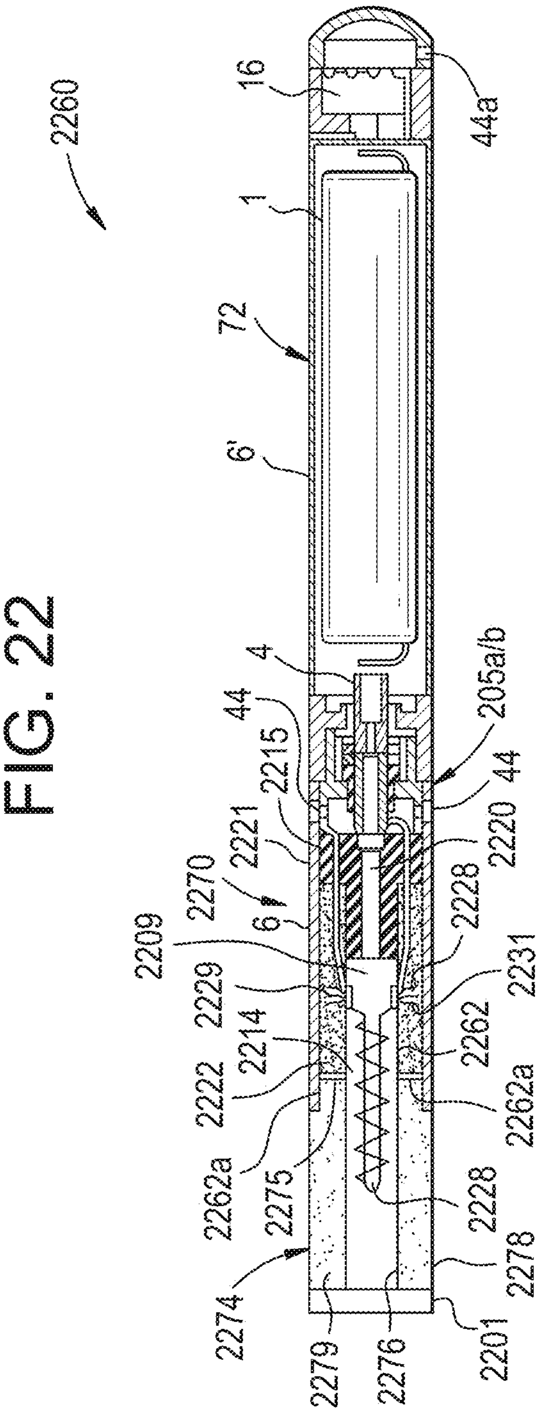
FIG. 22 is a cross-sectional view of the non-combustible smoking device of FIG. 1A.

FIG. 22 is a cross-sectional view of the non-combustible smoking device of FIG. 1A. As shown, the replaceable cartridge 2270 and the reusable fixture 72 are coupled together at the connection 205*a/b*. The reusable fixture 72 has been previously described. Therefore, the reusable fixture 72 will not be further described, for the sake of brevity.

The first section 2270 includes the outer tube 6 (or housing) extending in a longitudinal direction and an inner tube 2262 coaxially positioned within the outer tube or housing 6. The inner tube 2262 defines a portion of an outer air passage (or channel) 2209.

A portion 2275 of the tobacco containing section 2274 fits within a circumference defined by an inner portion of the outer tube 6 to create a frictional connection between the tobacco containing section 2274 and the cartridge 2270. Example embodiments are not limited to the frictional connection and other connections may be used. Thus, the tobacco containing section 2274 is a detachable insert.

The tobacco containing section 2274 includes an inner tube 2276 and an outer wall 7228. The inner tube 2276 of the tobacco containing section 2274 defines another portion of the outer air passage 2209. The outer wall 2278 and the inner tu22*e* 76 define a space (annulus) therebetween.

Figure 26:
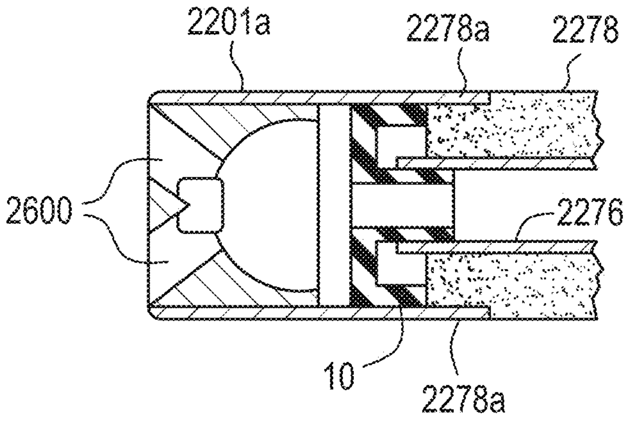
FIG. 26 illustrates an example embodiment of an end of the tobacco containing section of FIG. 22.
Figure 27:
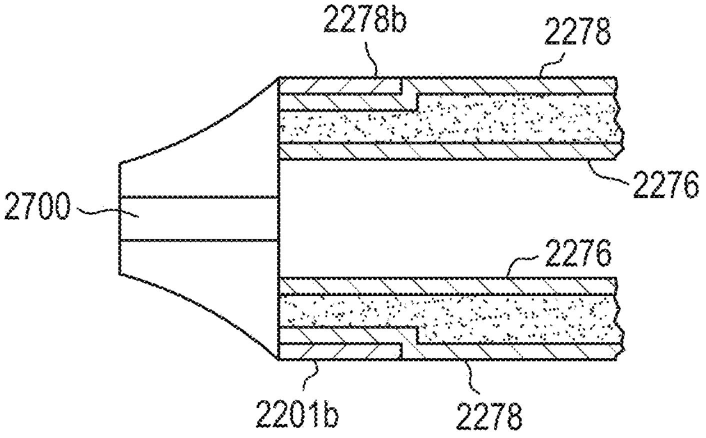
FIG. 27 illustrates an example embodiment of an end of the tobacco containing section of FIG. 22.
Figure 28:
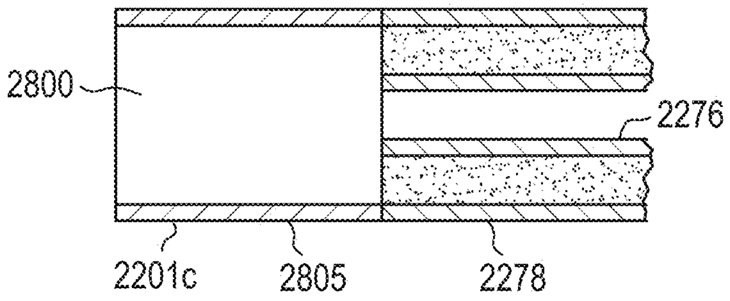
FIG. 28 illustrates an example embodiment of an end of the tobacco containing section of FIG. 22.

An end 2201 of the tobacco containing section 2274 may be a low efficiency cellulose acetate filter, a hollow acetate tube, or a plastic or wood mouthpiece. When the end 2201 is a plastic or wood mouthpiece, the end 2201 is shaped such that a portion of the outer wall 2278 fits within a circumference of the end 2201. FIGS. 26-28 illustrate example embodiments of the end 201.

Within the space between the outer wall 2278 and the inner tube 2276, the tobacco containing section 2274 includes a tobacco element 2279.

In addition, the inner tube 2276 and the outer wall 2278 may contain tipping paper, a tobacco plant material in any form including rolled natural or reconstituted tobacco leaf or sheet or from an annular piece made of tobacco filler or extruded tobacco in the shape of a sleeve. The inner tube 2276 and the outer wall 2278 may be made of the same or different materials.

In an example embodiment, the tobacco containing section 2274 may be a filtered cigarette, a non-filtered cigarette, a cigarillo, a filter tipped cigar filter, a tipped cigar or an untipped cigar/cigarillo, for example. However, example embodiments are not limited thereto. If the tobacco containing section 2274 is a shortened cigarette, the tobacco containing section 2274 may include a filter at the end 2201. In example embodiments where the tobacco insert is an untipped cigar/cigarillo, the tobacco insert does not include a filter.

The filter may be a low efficiency cellulose acetate (CA) filter. CA filter elements, such as triacetin, can be eluted into vapor. Vapor phase nicotine and other volatile elements in vapor can be reduced by a presence of tobacco.

A heater 2214 extends in a longitudinal direction from the inner tube 2262 into the inner tube 2276 in the outer air passage 2209.

The non-combustible smoking device 2260 can also include a central air passage 2220 defined in part by the inner tube 2262 and an upstream seal 2215. Moreover, the non-combustible smoking device 2260 includes a pre-vapor formulation supply reservoir 2222. The pre-vapor formulation supply reservoir 2222 comprises a pre-vapor formulation material and optionally a pre-vapor formulation storage medium 2221 operable to store the pre-vapor formulation material therein.

In an embodiment, the pre-vapor formulation supply reservoir 2222 is contained in an outer annulus between the outer tube 6 and the inner tube 2262. The annulus is sealed at an upstream end by the seal 2215. At a downstream end, the annulus is sealed by a gasket 2262*a*. The gasket 2262*a* may be a ring shaped gasket.

The gasket 2262*a* is placed on the pre-vapor formulation supply reservoir 2222 to seal the pre-vapor formulation in the pre-vapor formulation supply reservoir 2222 and prevent the tobacco element 2279 from mixing with the pre-vapor formulation.

In an embodiment, the heater 2214 is also contained in the inner tube 2262 downstream of and in spaced apart relation to the portion of central air passage 2220 defined by the seal 2215. The heater 2214 can be in the form of a wire coil, a planar body, a ceramic body, a single wire, a cage of resistive wire or any other suitable form.

A wick 2228 is in communication with the pre-vapor formulation material in the pre-vapor formulation supply reservoir 2222 and in communication with the heater 2214 such that the wick 2228 disposes pre-vapor formulation material in proximate relation to the heater 2214. The wick 2228 may be constructed of a fibrous and flexible material. The wick 2228 may include at least one filament having a capacity to draw a pre-vapor formulation. For example, the wick 2228 may comprise a bundle of filaments which may include glass (or ceramic) filaments. In another embodiment, a bundle comprising a group of windings of glass filaments, for example, three of such windings, all which arrangements are capable of drawing pre-vapor formulation via capillary action via interstitial spacing between the filaments.

The power supply 1 may be operably connected to the heater 2214 (for example, as described with respect to FIG. 1B) to apply voltage across the heater 2214. The non-combustible smoking device 2260 also includes at least one air inlet 44 operable to deliver air to the central air passage 2220 and/or other portions of the inner tube 2262.

Moreover, the heater 2214 extends in the longitudinal direction and heats the pre-vapor formulation material to a temperature sufficient to vaporize the pre-vapor formulation material and form a vapor when a negative pressure is applied to the end 2201. In other embodiments, the heater 2214 may be arranged in another manner such as in a direction transverse to the longitudinal direction.

The vapor then flows through the inner tube 2276 and into the tobacco element 2279 upon a negative pressure being applied at the end 2201 of the tobacco containing section 2274. The heater 2214 may be a set distance from the tobacco element 2279 such that the heater 2214 heats the tobacco element 2279 when a negative pressure is applied. For example, the heater 2214 may be ten (10) millimeters or less from the inner tube 2276.

The heater 2214 may extend into the tobacco containing portion 2274 between 5-20 millimeters. The heater 2214 may be arranged to produce a temperature of 50 degrees Celsius at the end 2201. Moreover, the heater 2214 may heat the tobacco element 2279 to a temperature between 50 and 200 degrees Celsius and heat the pre-vapor formulation at 300-350 degrees Celsius.

The heater 2214 warms the tobacco element 2279, but does not burn the tobacco. Thus, the warming of the tobacco element 2279 may be referred to as non-combustible. Because the section 2270 includes the heater 2214 and the tobacco containing section 2274 includes the tobacco element 2279, the sections 2270 and 2274 may jointly be referred to as a non-combustible smoking element.

In one embodiment, the first section (the cartridge) 2270 and the tobacco containing section 2274 are disposable. The downstream section 2270 can be replaced when the pre-vapor formulation supply reservoir 2222 is used up.

In an embodiment, the at least one air inlet 44 includes one or two air inlets. Alternatively, there may be three, four, five or more air inlets. If there is more than one air inlet 44, the air inlets 44 are located at different locations along the non-combustible smoking device 2260. At least one additional air inlet 44 can be located adjacent and upstream of the seal 2215 or at any other desirable location. Altering the size and number of air inlets 44 can also aid in establishing the resistance to draw of the non-combustible smoking device 2260.

In an embodiment, the heater 2214 is arranged to communicate with the wick 2228 and to heat the pre-vapor formulation material contained in the wick 2228 to a temperature sufficient to vaporize the pre-vapor formulation material and form a vapor.

The heater 2214 may be a wire coil surrounding the wick 2228. Examples of suitable electrically resistive materials include titanium, zirconium, tantalum and metals from the platinum group. Examples of suitable metal alloys include stainless steel, nickel-, cobalt-, chromium-, aluminium- titanium- zirconium-, hafnium-, niobium-, molybdenum-, tantalum-, tungsten-, tin-, gallium-, manganese- and iron-containing alloys, and super-alloys based on nickel, iron, cobalt, stainless steel. For example, the heater may be formed of nickel aluminides, a material with a layer of alumina on the surface, iron aluminides and other composite materials, the electrically resistive material may optionally be embedded in, encapsulated or coated with an insulating material or vice-versa, depending on the kinetics of energy transfer and the external physicochemical properties required. In one embodiment, the heater 2214 comprises at least one material selected from the group consisting of stainless steel, copper, copper alloys, nickel-chromium alloys, superalloys and combinations thereof. In an embodiment, the heater 2214 is formed of nickel-chromium alloys or iron-chromium alloys. In one embodiment, the heater 2214 can be a ceramic heater having an electrically resistive layer on an outside surface thereof.

In another embodiment, the heater 2214 may be constructed of an iron-aluminide (e.g., FeAl or Fe.sub.3Al), such as those described in commonly owned U.S. Pat. No. 5,595,706 to Sikka et al. filed Dec. 29, 1994, or nickel aluminides (e.g., Ni.sub.3Al). FeAl exhibits a resistivity of approximately 180 micro-ohms, whereas stainless steel exhibits approximately 50 to 91 micro-ohms. The higher resistivity lowers current draw or load on the power supply (battery) 1.

In one embodiment, the heater 2214 comprises a wire coil which at least partially surrounds the wick 2228. In that embodiment, the wire may be a metal wire and/or the heater coil that extends partially along the length of the wick 2228. The heater coil may extend fully or partially around the circumference of the wick 2228. In another embodiment, the heater coil is not in contact with the wick 2228.

The heater 2214 heats the pre-vapor formulation in the wick 2228 by thermal conduction. Alternatively, heat from the heater 2214 may be conducted to the pre-vapor formulation by means of a heat conductive element or the heater 2214 may transfer heat to the incoming ambient air that is drawn through the non-combustible smoking device 2260 during use, which in turn heats the pre-vapor formulation by convection.

In one embodiment, the wick 2228 comprises a ceramic material or ceramic fibers and may include any material described with respect to the wick 28. As noted above, the wick 2228 is at least partially surrounded by the heater 2214. Moreover, in an embodiment, the wick 2228 extends through opposed openings in the inner tube 2262 such that end portions 2229, 2231 of the wick 2228 are in contact with the pre-vapor formulation supply reservoir 2222.

The wick 2228 may comprise a plurality or bundle of filaments. In one embodiment, the filaments may be generally aligned in a direction transverse to the longitudinal direction of the non-combustible smoking device 2260 at the inner tube 2262 and generally in the longitudinal direction in the channel 2209, but example embodiments are not limited to this orientation. In one embodiment, the structure of the wick 2228 is formed of ceramic filaments capable of drawing the pre-vapor formulation via capillary action via interstitial spacing between the filaments to the heater 2214. The wick 2228 can include filaments having a cross-section which is generally cross-shaped, clover-shaped, Y-shaped or in any other suitable shape.

Instead of using a wick, the heater 2214 can be a porous material of sufficient capillarity and which incorporates a resistance heater formed of a material having a high electrical resistance capable of generating heat quickly.

In one embodiment, the wick 2228 and the pre-vapor formulation storage medium 2221 of the pre-vapor formulation supply reservoir 2222 are constructed from an alumina ceramic. In another embodiment, the wick 2228 includes glass fibers and the pre-vapor formulation storage medium 2221 includes a cellulosic material or polyethylene terephthalate.

In an embodiment, the power supply 1 may include a battery arranged in the non-combustible smoking device 2260 such that the anode is downstream of the cathode. The anode connector 4 contacts the downstream end of the battery. The heater 2214 is connected to the battery by two spaced apart electrical leads.

Figure 25:
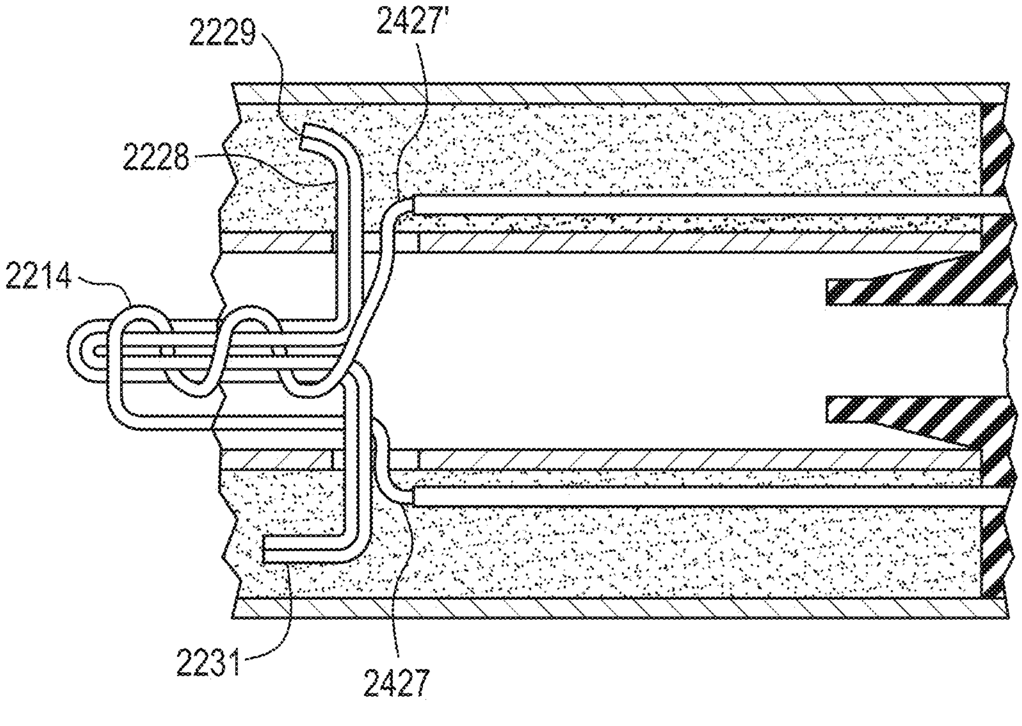
FIG. 25 is an enlarged view of a heater of the non-combustible smoking device of FIG. 22.

The connection between the uncoiled, end portions 2427, 2427' (see FIG. 25) of the heater 2214 and the electrical leads are highly conductive and temperature resistant while the heater 2214 is highly resistive so that heat generation occurs primarily along the heater 2214 and not at the contacts. The end portion 2427 is connected to the anode connector 4 and the end portion 2427' is connected to the cathode through the outer tube 6.

The non-combustible smoking device 2260 also includes control circuitry including the sensor 16. The sensor 16 is operable to sense an air pressure drop and initiate application of voltage from the power supply 1 to the heater 2214.

When activated, the heater 2214 heats a portion of the wick 2228 surrounded by the heater for less than about 10 seconds, more preferably less than about 7 seconds. Thus, the power cycle can range in period from about 2 seconds to about 10 seconds (e.g., about 3 seconds to about 9 seconds, about 4 seconds to about 8 seconds or about 5 seconds to about 7 seconds).

In an embodiment, the pre-vapor formulation supply reservoir 2222 includes the pre-vapor formulation storage medium 2221 containing pre-vapor formulation material. In FIG. 22, the pre-vapor formulation supply reservoir 2222 is contained in an outer annulus between inner tube 2262 and outer tube 6 and between gasket 2262 and the seal 2215. Thus, the pre-vapor formulation supply reservoir 2222 at least partially surrounds the central air passage 2220 and the heater 2214 and the wick 2228 extend between portions of the pre-vapor formulation supply reservoir 2222.

The pre-vapor formulation storage medium 2221 may be a fibrous material comprising cotton, polyethylene, polyester, rayon and combinations thereof. The fibers may have a diameter ranging in size from about 6 microns to about 15 microns (e.g., about 8 microns to about 12 microns or about 9 microns to about 11 microns). The pre-vapor formulation storage medium 2221 may be a sintered, porous or foamed material. Also, the fibers may be sized to be irrespirable and can have a cross-section which has a y shape, cross shape, clover shape or any other suitable shape.

In another example embodiment, the pre-vapor formulation storage medium 2221 may be a tobacco filler or tobacco slurry.

Also, the pre-vapor formulation material has a boiling point suitable for use in the non-combustible smoking device 2260. If the boiling point is too high, the heater 2214 will not be able to vaporize the pre-vapor formulation in the wick 2228. However, if the boiling point is too low, the pre-vapor formulation may vaporize without the heater 2214 being activated.

In operation, with non-combustible smoking device 2260 in an assembled configuration, a negative pressure may be applied on the end 2201. This may cause an internal pressure drop inside non-combustible smoking device 2260 that may cause an inlet air flow to enter device 2260 via air inlets 44/44*a*. The internal pressure drop may also cause an internal pressure drop within section 72 as air is drawn through air inlet 44*a* (via an air flow path traveling through section 72). The internal pressure drop formed in section 72 may be sensed by sensor 16. The sensor 16 may then operate to close an electrical circuit that includes the power supply 1. In turn, electrical leads carry an electrical current to heater 2214 in order to energize the heater 2214. The energized heater 2214 in turn heats and vaporizes the pre-vapor formulation material that is drawn toward the heater 2214 via the wick 2228.

The pre-vapor formulation material is transferred from the pre-vapor formulation supply reservoir 2222 and/or pre-vapor formulation storage medium 2221 in proximity of the heater 2214 by capillary action in the wick 2228. In one embodiment, the wick 2228 has a first end portion 2229 and a second opposite end portion 2231. The first end portion 2229 and the second end portion 2231 extend into opposite sides of the pre-vapor formulation storage medium 2221 for contact with pre-vapor formulation material contained therein. The heater 2214 at least partially surrounds a central portion of the wick 2228 such that when the heater 2214 is activated, the pre-vapor formulation in the central portion of the wick 2228 is vaporized by the heater 2214 to vaporize the pre-vapor formulation material and form vapor. Due to a negative pressure being applied, the vapor flows from the heater 2214, through the tobacco element 2279 and out of the end 2201.

The vapor may elute tobacco elements into the flow stream. Some thermal reactions may also be present between the vapor and the tobacco element.

One advantage of an embodiment is that the pre-vapor formulation material in the pre-vapor formulation supply reservoir 2222 is protected from oxygen (because oxygen cannot generally enter the pre-vapor formulation storage portion via the wick) so that the risk of degradation of the pre-vapor formulation material is significantly reduced. Moreover, in some embodiments in which the outer tube 6 is not clear, the pre-vapor formulation supply reservoir 2222 is protected from light so that the risk of degradation of the pre-vapor formulation material is significantly reduced. Thus, a high level of shelf-life and cleanliness can be maintained.

The arrangement of the section 2270 is not limited to the embodiment shown in FIG. 22 and may include other modifications such as those described in U.S. patent application Ser. No. 14/572,360, the entire contents of which are hereby incorporated by reference.

The inner tube 2262 may be formed of any suitable material or combination of materials. Examples of suitable materials include metals, alloys, plastics or composite materials containing one or more of those materials, or thermoplastics that are suitable for food or pharmaceutical applications, for example polypropylene, polyetheretherketone (PEEK), ceramic, and polyethylene. In one embodiment, the material is light and non-brittle.

While FIG. 22 illustrates the tobacco containing section 2274 having a singular annular sleeve, example embodiments are not limited thereto.

Figure 23A:
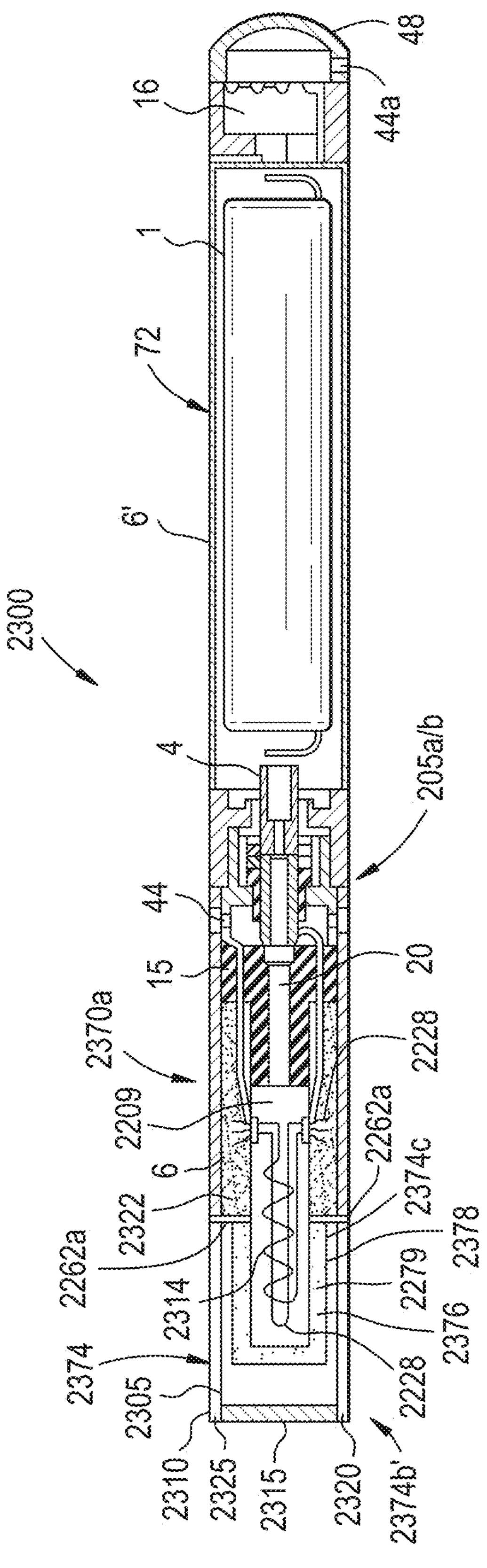
FIG. 23A illustrates an example embodiment of a non-combustible smoking device including a tobacco containing section having annular sleeves.

FIG. 23A illustrates an example embodiment of a non-combustible smoking device including a tobacco containing section 2374 having annular sleeves 2374*a* and 2374*b*. A non-combustible smoking device 2300 is similar to the non-combustible smoking device 2260. Thus, for the sake of brevity, only the differences will be described.

In FIG. 23A, a tobacco containing section 2374 includes annular sleeves 2374*a* and 2374*b*.

The annular sleeve 2374*a* includes an inner tube 2376 and an outer wall 2378. The inner tube 2376 defines another portion of the outer air passage 2209. The outer wall 2378 and the inner tube 2376 define a space (annulus) therebetween. The outer wall 2378 and the inner tube 2376 may be made of the same materials of the outer wall 2278 and inner tube 2276, respectively.

Within the space between the outer wall 2378 and the inner tube 2376 is the tobacco element 2279.

Figure 24:
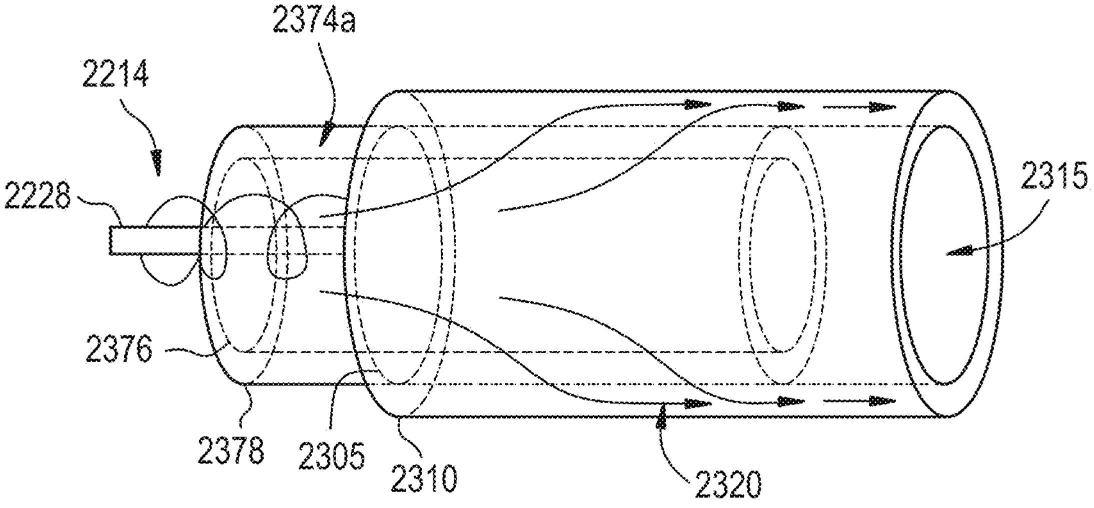
FIG. 24 illustrates an air flow pattern of the non-combustible smoking device shown in FIG. 23A.

The annular sleeve 2374*b* includes an inner tube 2305 and an outer wall 2310. As shown in FIG. 23A, the annular sleeve 2374*b* encompasses the annular sleeve 2374*a*. The inner tube 2305 is permeable and the outer wall 2310 is impermeable. An end 2315 of the annular sleeve 2374*b* is closed to air flow. The end 2315 may be made of any material that acts as a plug to block airflow such as a plastic (e.g., polyethalane) or a metal. Thus, air flows from the air passage 2209, through the annular sleeve 2374*a* through the inner tube 2305 and into air channels 2320, 2325 upon applying a negative pressure to the tobacco containing section 2374, as shown in FIG. 24.

The inner tube 2305 is a permeable material such as a membrane, mesh, perforated plastic or paper. The inner tube 305 is made of a material that maintains the structural integrity of the annular sleeve 2374*b*. The outer wall 2310 is an impermeable material such as a plastic.

Figure 23B:
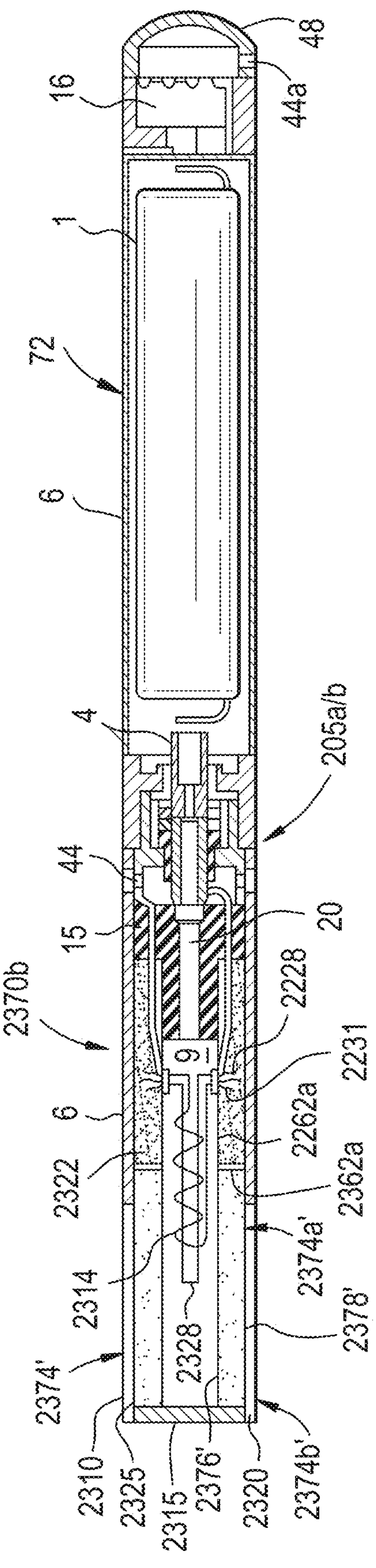
FIG. 23B illustrates an example embodiment of a non-combustible smoking device including a tobacco containing section having annular sleeves.

FIG. 23B illustrates another example embodiment of a non-combustible smoking device including a tobacco containing section 2374' having annular sleeves 2374*a*' and 2374*b*'.

The tobacco containing section 2374' is similar to the tobacco containing section 2374. Thus, only the differences will be described.

In FIG. 23B, an annular sleeve 2374*b*' does not include the inner tube 2305. Instead, an outer wall 2378' of the annular sleeve 2374*a*' is also part of the annular sleeve 2374*b*'. With an inner tube 2376', the outer wall 2378' and the inner tube 2376' define a space (annulus) therebetween.

Within the space between the outer wall 2378' and the inner tube 2376' is the tobacco element 2279.

As shown in FIG. 23B, the outer wall 2378' and the inner tube 2376' extend to the end 2315. The outer wall 2378' and the inner tube 2376' may be made of the same materials as the outer wall 2378 and the inner tube 2376, respectively.

Figure 23C:
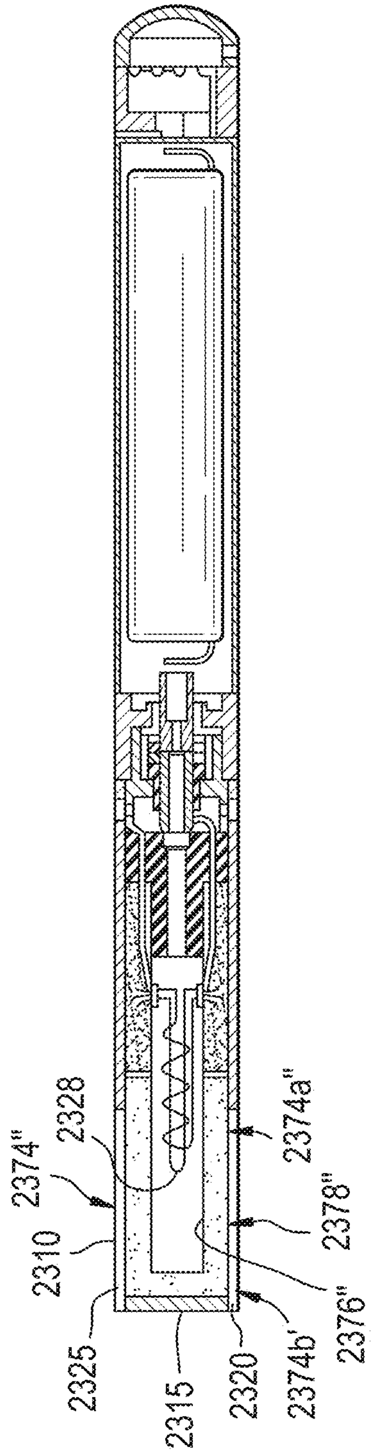
FIG. 23C illustrates an example embodiment of a non-combustible smoking device including a tobacco containing section having annular sleeves.

FIG. 23C illustrates another example embodiment of a non-combustible smoking device including a tobacco containing section 2374".

The tobacco containing section 2374" is similar to the tobacco containing section 2374'. Thus, only the differences will be described.

In FIG. 23B, an inner tube 2376" of an annular sleeve 2374*a*" is closed off before the end 2315. A space is then defined between the end 2315 and the inner tube 2376". Tobacco element 2279 is also between the end 2315 and the inner tube 2376".

The non-combustible smoking devices according to example embodiments are effective in heating the tobacco and distilling and eluting tobacco specific flavors because of their flow pattern and proximity of the tobacco element to the heater 2214 (vapor forming area). The perpendicular flow, shown in FIG. 24, of the vapor from the heater 2214 to the tobacco element and the closeness of the tobacco to the heater 2214 allow for effective heating of the tobacco and subsequent distillation and elution of volatile tobacco flavors.

While example embodiments illustrate that vapor can exit the non-combustible smoking device in an annular fashion, it should be understood that the vapor may exit in a concentric fashion.

FIG. 26 illustrates an example embodiment of an end of the tobacco containing section 2274 being a plastic mouthpiece. As shown in FIG. 26, an end 2201*a* has at least two off-axis, diverging outlets 2600. The end 2201*a* is in fluid communication with the central air passage 2209, which extends through the gasket 10. The gasket 10 is at a downstream end of the tobacco containing section 2274 so as to prevent leakage of the tobacco material into the end 2201*a*.

A portion of the outer wall 2278*a* fits within a circumference of the end 2201*a*.

Due to a negative pressure being applied to the tobacco containing section 2274, the vapor flows from the heater 2214, through the tobacco containing section 2274 and out of the end 2201*a*.

FIG. 27 illustrates an example embodiment of an end of the tobacco containing section 2274.

An end 2201*b* fits over a portion of the outer wall 2278*b*. A negative pressure may be applied on the end 2201*b*. Due to the negative pressure, the vapor flows from the heater 2214, out of the tobacco containing section 2274 through an air passage 2700.

FIG. 28 illustrates an example embodiment of an end of the tobacco containing section 2274.

An end 2201*c* includes a filter 2800. In example embodiments where the tobacco insert is an untipped cigar/cigarillo, the tobacco insert does not include a filter.

Tipping paper 2805 may overlap the filter 2800. Tipping paper may also be used as the wall 2278. Thus, the tipping paper 2805 provides stiffness to the tobacco containing section 2274, permitting easier insertion to the cartridge 2270. An aluminum foil may also be used to contain the tobacco element, with or without additional tipping paper.

In the example shown in FIG. 28, the filter 2800 may be a cellulose acetate (CA) filter. CA filter elements, such as triacetin, can be eluted into vapor. Vapor phase nicotine and other volatile elements in vapor can be reduced by a presence of tobacco.

When a negative pressure is applied to the tobacco containing section 2274, the vapor flows from the heater 2214, through the tobacco containing section 2274 and out of the filter 2800.

Example embodiments provide a non-combustible smoking device having a heater that heats a pre-vapor formulation and may provide heat to a tobacco element. More specifically, the non-combustible smoke device according to example embodiments exposes a vapor to a tobacco element and/or exposes a pre-vapor formulation to a tobacco element. When the tobacco element is in the pre-vapor formulation the physical integrity of the tobacco element is preserved.

In other example embodiments, a non-combustible smoke device can be a pod device or tank device that exposes a vapor to a tobacco element and/or exposes a pre-vapor formulation to a tobacco element.

While a single heater is described with reference to FIGS. 22-28, example embodiments may include a multiple heater non-combustible smoking device. A first heater may be the heater 2214 to vaporize the pre-vapor formulation and a second heater may be used to heat the tobacco element. The second heater may penetrate the tobacco element.

In other example embodiments, a non-combustible smoking device includes more than two heaters.

Example embodiments having thus been described, it will be obvious that the same may be varied in many ways. Such variations are not to be regarded as a departure from the intended spirit and scope of example embodiments, and all such modifications as would be obvious to one skilled in the art are intended to be included within the scope of the following claims.

What is claimed is:

1. A non-combustible smoking element comprising:
- a pre-vapor formulation reservoir configured to contain a pre-vapor formulation material;
- a pre-vapor heater coupled to the pre-vapor formulation reservoir and configured to heat at least a portion of the pre-vapor formulation material into a vapor;
- a plurality of tobacco heaters configured to provide heat to at least a portion of tobacco, the tobacco including at least one of a tobacco leaf, a tobacco plug, a reconstituted tobacco, a compressed tobacco rod, or a powder; and
- a tobacco housing configured to contain the tobacco, the tobacco housing and the plurality of tobacco heaters being upstream from the pre-vapor heater, the tobacco housing including,
  - an inner wall extending in a longitudinal direction of the non-combustible smoking element, and
  - an outer wall around the inner wall and extending in the longitudinal direction, the outer wall defining an annular housing around the inner wall, the annular housing configured to contain the tobacco and the plurality of tobacco heaters.

2. The non-combustible smoking element of claim 1, wherein the plurality of tobacco heaters are upstream from the pre-vapor heater.

3. The non-combustible smoking element of claim 1, wherein the plurality of tobacco heaters are outside a channel and the pre-vapor heater is in the channel.

4. The non-combustible smoking element of claim 1, wherein at least one of the plurality of tobacco heaters is a coil and extends around the inner wall.

5. The non-combustible smoking element of claim 4, wherein at least one of the plurality of tobacco heaters extends around the inner wall at an interval of 1-2 millimeters.

6. The non-combustible smoking element of claim 4, wherein the tobacco housing includes, a connecting piece at a first end of the tobacco housing, the connecting piece including at least one first air inlet to provide air to the annular housing.

7. The non-combustible smoking element of claim 6, wherein the connecting piece includes, a second air inlet to provide air within the inner wall.

8. The non-combustible smoking element of claim 1, wherein at least one of the plurality of tobacco heaters is soldered to a first wire connected to a cathode portion.

9. A non-combustible smoking element comprising:

a pre-vapor formulation reservoir configured to contain a pre-vapor formulation material; and a heater coupled to the pre-vapor formulation reservoir and configured to heat at least a portion of the pre-vapor formulation material into a vapor and provide the vapor to a first portion of a channel, wherein a second portion of the channel is configured to contain tobacco and is positioned to receive the vapor, wherein the heater is in the channel and the tobacco is downstream from the heater, the pre-vapor formulation reservoir includes an inner wall defining the channel and an outer wall surrounding the inner wall to define an annular housing, the annular housing configured to contain the pre-vapor formulation material, and the second portion of the channel is between the heater and an end of the inner wall.

10. The non-combustible smoking element of claim 9, wherein the heater is configured to heat the tobacco at a maximum of 200 degrees Celsius.

11. The non-combustible smoking element of claim 9, wherein the heater is separated from the tobacco by less than thirty millimeters.

12. The non-combustible smoking element of claim 9, wherein the pre-vapor formulation reservoir is configured to surround the second portion of the channel that contains the tobacco.

13. The non-combustible smoking element of claim 9, further comprising:

a wick in communication with the pre-vapor formulation reservoir and with the heater.

14. A non-combustible smoking element comprising:

a pre-vapor formulation reservoir configured to contain a pre-vapor formulation material;

a heater coupled to the pre-vapor formulation reservoir, the heater configured to simultaneously provide heat to tobacco and to vaporize at least a portion of the pre-vapor formulation material into a vapor and provide the vapor to a first channel;

a tobacco housing configured to contain the tobacco and defining at least a portion of the first channel, the tobacco housing overlapping at least a portion of the heater, the tobacco housing being arranged to receive the vapor, the heater extending in a longitudinal direction of the tobacco housing; and an outer wall on the tobacco housing, the outer wall including a cover covering the first channel.

15. The non-combustible smoking element of claim 14, wherein the tobacco housing includes an inner wall and an outer wall, the inner wall being permeable and the outer wall being impermeable.

16. The non-combustible smoking element of claim 14, wherein the outer wall includes, an outer wall part, and an inner wall part, the outer wall part and the tobacco housing defining portions of a second air channel.

17. The non-combustible smoking element of claim 16, wherein the cover is at a first end of the inner wall part.

* * * * *